United States Patent
Row et al.

(10) Patent No.: US 10,907,637 B2
(45) Date of Patent: *Feb. 2, 2021

(54) CUFF FOR AIR DELIVERY CONDUIT

(71) Applicant: ResMed Pty Ltd, Bella Vista (AU)

(72) Inventors: Nathan John Row, Sydney (AU); Alexander Virr, Gosford (AU); Nicholas Andrew Earl, Essex (GB)

(73) Assignee: ResMed Pty Ltd, Bella Vista (AU)

( * ) Notice: Subject to any disclaimer, the term of this patent is extended or adjusted under 35 U.S.C. 154(b) by 382 days.

This patent is subject to a terminal disclaimer.

(21) Appl. No.: 15/876,557

(22) Filed: Jan. 22, 2018

(65) Prior Publication Data

US 2018/0142690 A1 May 24, 2018

Related U.S. Application Data

(63) Continuation of application No. 12/461,967, filed on Aug. 28, 2009, now Pat. No. 9,903,371.

(60) Provisional application No. 61/202,907, filed on Apr. 17, 2009, provisional application No. 61/097,765, filed on Sep. 17, 2008.

(51) Int. Cl.
*A61M 16/08* (2006.01)
*F04D 1/00* (2006.01)

(52) U.S. Cl.
CPC ........... *F04D 1/00* (2013.01); *A61M 16/0816* (2013.01); *A61M 16/0875* (2013.01)

(58) Field of Classification Search
CPC ............ A61M 16/816; A61M 16/0875; A61M 39/10; A61M 2039/1027; F16L 37/02; F16L 25/10

See application file for complete search history.

(56) References Cited

U.S. PATENT DOCUMENTS

| | | | |
|---|---|---|---|
| 2,073,335 | A | 3/1937 | Connell |
| 2,516,864 | A | 8/1950 | Gilmore |
| 3,388,705 | A | 6/1968 | Grosshandler |
| 4,188,081 | A | 2/1980 | Holden et al. |
| 4,437,691 | A | 3/1984 | Laney |
| 4,621,632 | A | 11/1986 | Bartels et al. |
| 4,714,279 | A | 12/1987 | Custeau |
| 5,054,156 | A | 10/1991 | Watanabe et al. |
| 5,309,902 | A | 5/1994 | Kee et al. |
| 5,336,192 | A | 8/1994 | Palestrant |
| 5,382,242 | A | 1/1995 | Horton et al. |
| 5,392,770 | A | 2/1995 | Clawson et al. |

(Continued)

FOREIGN PATENT DOCUMENTS

| | | |
|---|---|---|
| EP | 1 369 141 | 12/2003 |
| EP | 1 741 462 A1 | 1/2007 |

(Continued)

OTHER PUBLICATIONS

Proceeding Correspondence issued in corresponding New Zealand Application No. 625795 on Apr. 10, 2018, (1 page).

(Continued)

*Primary Examiner* — Margaret M Luarca

(74) *Attorney, Agent, or Firm* — Nixon & Vanderhye P.C.

(57) ABSTRACT

A cuff for an air delivery conduit includes a first end portion provided to a tube and a second end portion adapted to engage a tubular connector. The second end portion includes an annular bead for sealing and retention.

33 Claims, 29 Drawing Sheets

(56) References Cited

U.S. PATENT DOCUMENTS

| | | | |
|---|---|---|---|
| 5,429,398 | A | 7/1995 | Lupke |
| 5,640,951 | A | 6/1997 | Huddart et al. |
| 5,762,382 | A | 6/1998 | Pernetti |
| 6,078,730 | A | 6/2000 | Huddart et al. |
| 6,099,046 | A | 8/2000 | Oh |
| 6,267,416 | B1 * | 7/2001 | Ferreira ............... F16L 37/008 285/319 |
| 6,272,933 | B1 | 8/2001 | Gradon et al. |
| 6,691,707 | B1 | 2/2004 | Gunaratnam et al. |
| 6,892,729 | B2 | 5/2005 | Smith et al. |
| 6,953,354 | B2 | 10/2005 | Edirisuriya |
| 7,226,302 | B2 | 6/2007 | Walter et al. |
| 7,306,205 | B2 | 12/2007 | Huddart et al. |
| 7,814,907 | B2 | 10/2010 | Bremner et al. |
| D629,891 | S | 12/2010 | Virr |
| D629,892 | S | 12/2010 | Hill |
| 7,874,292 | B2 | 1/2011 | Smith et al. |
| D634,406 | S | 3/2011 | Kilmas |
| D638,537 | S | 5/2011 | Virr |
| D641,467 | S | 7/2011 | Amann |
| D652,916 | S | 1/2012 | Row et al. |
| 8,100,127 | B2 | 1/2012 | Worley |
| 8,360,059 | B2 | 1/2013 | Koulechov et al. |
| 8,770,198 | B2 | 7/2014 | Yee |
| 8,783,298 | B2 | 7/2014 | Zucker et al. |
| 8,905,031 | B2 | 12/2014 | Barlow |
| D736,371 | S | 8/2015 | Row et al. |
| 2003/0236015 | A1 | 12/2003 | Edirisuriya et al. |
| 2004/0079370 | A1 | 4/2004 | Gradon |
| 2006/0118113 | A1 | 6/2006 | Bremner et al. |
| 2007/0040378 | A1 | 2/2007 | Sheppard et al. |
| 2007/0218734 | A1 | 9/2007 | Walter et al. |
| 2007/0277828 | A1 | 12/2007 | Ho et al. |
| 2008/0028850 | A1 | 2/2008 | Payton et al. |
| 2008/0054635 | A1 | 3/2008 | Skiba et al. |
| 2008/0066756 | A1 | 3/2008 | Lang et al. |
| 2008/0077176 | A1 | 3/2008 | Hanlon et al. |
| 2008/0105257 | A1 | 5/2008 | Klasek et al. |
| 2009/0126817 | A1 | 5/2009 | Gray |
| 2010/0083965 | A1 | 4/2010 | Virr et al. |
| 2010/0116272 | A1 | 5/2010 | Row et al. |
| 2010/0236552 | A1 | 9/2010 | Kwok et al. |
| 2011/0023874 | A1 | 2/2011 | Bath |
| 2012/0227738 | A1 | 9/2012 | Virr |

FOREIGN PATENT DOCUMENTS

| | | |
|---|---|---|
| GB | 1030840 | 5/1966 |
| GB | 2 173 274 A | 10/1986 |
| WO | WO 2006/019323 | 2/2006 |
| WO | WO 2006/133480 | 12/2006 |
| WO | WO 2008095245 | 8/2008 |
| WO | WO 2009/0777045 | 6/2009 |
| WO | 2010/031126 | 3/2010 |
| WO | WO 2010/031126 A1 | 3/2010 |

OTHER PUBLICATIONS

Decision of Commissioner issued in corresponding New Zealand Application No. 625795 on Apr. 10, 2018, (14 pages).
Letter filed by Baldwins on behalf of Fisher & Paykel Healthcare Limited in New Zealand Application No. 625795 on Feb. 16, 2018, (1 page).
Statutory Declaration of Christian Dominic Adrian Way dated Feb. 16, 2018 and filed in New Zealand Application No. 625795, (3 pages).
Statutory Declaration of Robyn Christine Jackson dated Feb. 16, 2018 and filed in New Zealand Application No. 625795, (3 pages).
Proceeding Halt dated May 31, 2017 in related New Zealand Application No. 625795 (2 pages).
Second Amended Statement of Case dated May 11, 2017 in related New Zealand Application No. 625795, (clean and tracked) (31 pages).
Third Amended Notice of Opposition to Grant of Patent dated May 11, 2017 in related New Zealand Application No. 625795, (clean and tracked) (4 pages).
Deadline for Applicant to File Evidence dated Mar. 20, 2017 in related New Zealand Application No. 625795 (2 pages).
Deadline for Counterstatement issued in related NZ Application No. 625795 dated Jan. 7, 2016, along with Statement of Case and Amended Notice of Opposition, 16 pages.
Statutory Declaration of Anthony James Newland dated Feb. 7, 2017 in related New Zealand Application No. 625795. (8 pages).
Statutory Declaration of Louisa-Dawn Kiddie dated Mar. 6, 2017 in related New Zealand Application No. 625795 (5 pages).
Statutory Declaration of Peter Geoffrey Hawkins dated Mar. 7, 2017 in related New Zealand Application No. 625795 (8 pages).
Affirmation of Michael Richardson dated Mar. 6, 2017 in related New Zealand Application No. 625795 (6 pages).
Statutory Declaration of Anthony James Newland dated Mar. 14, 2017 in related New Zealand Application No. 625795 (24 pages).
Deadline for Opponent to File Evidence issued in related New Zealand Application No. 625795 dated Jul. 7, 2016, (2 pages).
U.S. Office Action (Notice of Allowance and Notice of Allowability) issued in related U.S. Appl. No. 29/543,373 dated Mar. 13, 2016, 21 pages.
Deadline for Counterstatement issued in related New Zealand Application No. 625795 dated Apr. 15, 2016, along with Second Amended Notice of Opposition, First Amended Statement of Case, and Document U1 (33 pages).
Office Action issued in related U.S. Appl. No. 29/506,929 dated Sep. 11, 2015 (10 pages).
Patent Examination Report No. 1 issued in related Australian Application No. 2014201737, dated May 18, 2015 (3 pages).
New Zealand Further Examination Report for NZ Appln. No. 597179, dated Apr. 10, 2013, 1 page.
Patent Examination Report issued in related Australian Application No. 2014201737, dated Nov. 18, 2015, (2 pages).
Notice of Opposition to Grant of Patent and Application Under Regulation 168 for Extension of Time issued in related New Zealand Application No. 625975, dated Oct. 27, 2015, (3 pages).
New Zealand Further Examination Report for NZ Application No. 597179, dated Apr. 10, 2013, 1 page.
New Zealand First Examination Report for NZ Application No. 605324, dated Jan. 7, 2013, 2 pages.
Australian Patent Examination Report No. 1 for AU Application No. 2009212880, dated Jan. 14, 2013, 2 pages.
New Zealand Examination Report issued in corresponding NZ Appln. No. 579384 (dated Feb. 4, 2011).
Examination Report issued in corresponding NZ Appln. No. 597179 (dated Dec. 20, 2011).
Examination Report issued in corresponding NZ Appln. No. 589766 (dated Mar. 12, 2012).
Row et al., U.S. Appl. No. 29/311,222, filed Jan. 22, 2009.
Virr et al., U.S. Appl. No. 29/311,183, filed Jan. 12, 2009.
Further Examination Report issued in corresponding New Zealand Application No. 625795 dated Sep. 8, 2014, 2 pages.
Proceeding Correspondence issued in New Zealand Application No. 625795, dated Dec. 21, 2017, 2 pages.
Statutory Declaration of Anthony James Newland filed in New Zealand Application No. 625795, dated Nov. 29, 2017, 10 pages.

* cited by examiner

CUFF FOR AIR DELIVERY CONDUIT

CROSS-REFERENCE TO APPLICATION

This application is a continuation of U.S. application Ser. No. 12/461,967, now U.S. Pat. No. 9,903,371, filed Aug. 28, 2009, which claims the benefit of U.S. Provisional Patent Application Nos. 61/097,765, filed Sep. 17, 2008, and 61/202,907, filed Apr. 17, 2009, each of which is incorporated herein by reference in its entirety.

FIELD OF THE INVENTION

The present invention relates to cuffs or connectors for air delivery conduits used in breathing apparatus for treatment, e.g., of Sleep Disordered Breathing (SDB) with Continuous Positive Airway Pressure (CPAP) or Non-Invasive Positive Pressure Ventilation (NIPPV).

BACKGROUND OF THE INVENTION

Breathing apparatus to deliver breathable gas to a patient typically includes a positive airway pressure (PAP) device, an optional humidifier, an air or gas delivery conduit, and a patient interface. In use, the air delivery conduit delivers pressurized air or gas from the flow generator and optional humidifier to the patient interface in contact with the patient's face.

Each end of the air delivery conduit includes a cuff or connector for connecting the air delivery conduit to the patient interface and PAP device/humidifier.

The present invention provides improvements to known cuffs to facilitate engagement, seal, and retention.

SUMMARY OF THE INVENTION

One aspect of the invention relates to a cuff for an air delivery conduit including a first end portion provided to a tube and a second end portion adapted to engage a tubular connector. The second end portion includes an entry surface that is curved or chamfered along its length to provide a lead in for inserting the second end portion onto the tubular connector in use. The entry surface provides an internal diameter that is larger than an external diameter of the tubular connector.

Another aspect of the invention relates to a cuff for an air delivery conduit including a first end portion provided to a tube and a second end portion adapted to engage a tubular connector. The second end portion includes an annular bead providing an internal diameter that is smaller than an external diameter of the tubular connector. The annular bead is structured to resiliently deform upon engagement with the tubular connector so as to provide a gas tight seal against the tubular connector and retain the cuff on the tubular connector. The bead has a width that is less than a maximum insertion distance of the cuff.

Another aspect of the invention relates to a cuff for an air delivery conduit including a first end portion provided to a tube and a second end portion adapted to engage a tubular connector. The second end portion includes a radial sealing lip along its opening that provides an internal diameter that is smaller than an external diameter of the tubular connector. The sealing lip is structured to resiliently deform upon engagement with the tubular connector so as to provide a gas tight seal against the tubular connector. The sealing lip provides a flexible protrusion structured to resiliently deflect from a first position and into a second position within a cut-out of the second end portion.

Another aspect of the invention relates to a cuff for an air delivery conduit including a first end portion provided to a tube and a second end portion adapted to engage a tubular connector. The second end portion includes a seal structure to provide a gas tight seal against the tubular connector and a retaining structure substantially independent from the seal structure to retain the cuff on the tubular connector.

Other aspects, features, and advantages of this invention will become apparent from the following detailed description when taken in conjunction with the accompanying drawings, which are a part of this disclosure and which illustrate, by way of example, principles of this invention.

BRIEF DESCRIPTION OF THE DRAWINGS

The accompanying drawings facilitate an understanding of the various embodiments of this invention. In such drawings:

FIGS. 11-1 to 11-3 are sequential views showing attachment of the cuff of FIG. 4 to a tubular connector;

DETAILED DESCRIPTION OF ILLUSTRATED EMBODIMENTS

The following description is provided in relation to several embodiments which may share common characteristics and features. It is to be understood that one or more features of any one embodiment may be combinable with one or more features of the other embodiments. In addition, any single feature or combination of features in any of the embodiments may constitute additional embodiments.

In this specification, the word "comprising" is to be understood in its "open" sense, that is, in the sense of "including", and thus not limited to its "closed" sense, that is the sense of "consisting only of". A corresponding meaning is to be attributed to the corresponding words "comprise", "comprised" and "comprises" where they appear.

The term "air" will be taken to include breathable gases, for example air with supplemental oxygen. It is also acknowledged that the PAP devices described herein may be designed to pump fluids other than air.

Also, it should be appreciated that reference to a "gas tight" seal may include a seal having an acceptable known leak rate.

1. CPAP System

Figure 1:
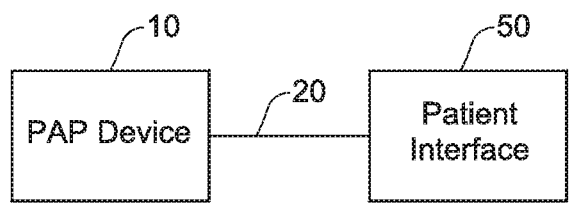
FIG. 1 is a schematic view of an embodiment of a CPAP system.

As schematically shown in FIG. 1, a PAP system (e.g., CPAP system) generally includes a PAP device 10, an air delivery conduit 20 (also referred to as a tube or tubing), and a patient interface 50. In use, the PAP device 10 generates a supply of pressurized air that is delivered to the patient via an air delivery conduit 20 that includes one end coupled to the outlet of the PAP device 10 and an opposite end coupled to the inlet of the patient interface 50. The patient interface comfortably engages the patient's face and provides a seal. The patient interface or mask may have any suitable configuration as is known in the art, e.g., full-face mask, nasal mask, oro-nasal mask, mouth mask, nasal prongs, etc. Also, headgear may be utilized to comfortably support the patient interface in a desired position on the patient's face.

Figure 2:
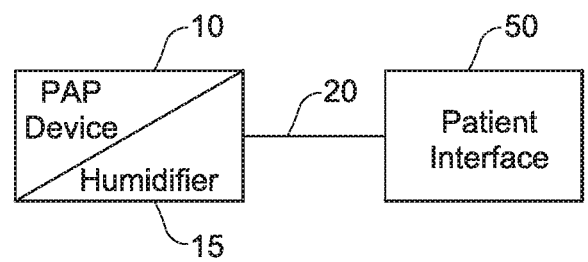
FIG. 2 is a schematic view of another embodiment of a CPAP system.

In embodiments, a humidifier may be incorporated or integrated into the PAP device or otherwise provided downstream of the PAP device. In such embodiments, the air delivery conduit 20 may be provided between the patient interface 50 and the outlet of the humidifier 15 as schematically shown in FIG. 2.

Figure 3:
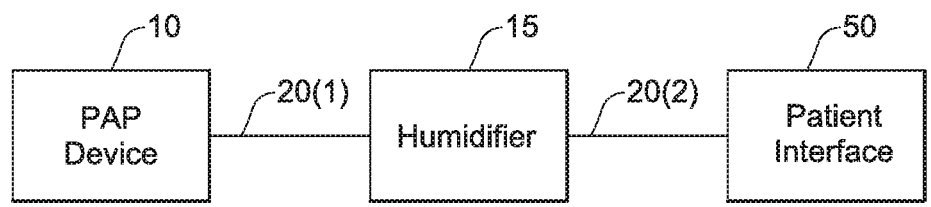
FIG. 3 is a schematic view of another embodiment of a CPAP system.

It should be appreciated that the air delivery conduit may be provided along the air delivery path in other suitable manners. For example, as schematically shown in FIG. 3, the humidifier 15 may be a separate component from the PAP device 10 so that an air delivery conduit 20(1) is placed between the PAP device 10 and the humidifier 15 and another air delivery conduit 20(2) is placed between the humidifier 15 and the patient interface 50.

Generally, a heated humidifier is used to provide sufficient humidity and temperature to the air so that the patient will be comfortable. In such embodiment, the air delivery conduit may be heated to heat the gas and prevent "rain-out" or condensation forming on the inside of the conduit as the gas is supplied to the patient. In this arrangement, the air delivery conduit may include one or more wires or sensors associated with heating.

As described below, each end of the air delivery conduit includes a cuff structured to attach the tube to the patient interface, PAP device, and/or humidifier. The cuffs differ for non-heated tubes and heated tubes, e.g., cuffs for heated tubes accommodate sensors or electronics/wiring associated with heating.

While the cuff is described as being implemented into a CPAP system of the type described above, it may be implemented into other tubing arrangements for conveying gas or liquid. That is, the CPAP system is merely exemplary, and aspects of the present invention may be incorporated into other suitable arrangements.

2. Cuffs for Non-Heated Tube

Figure 4:
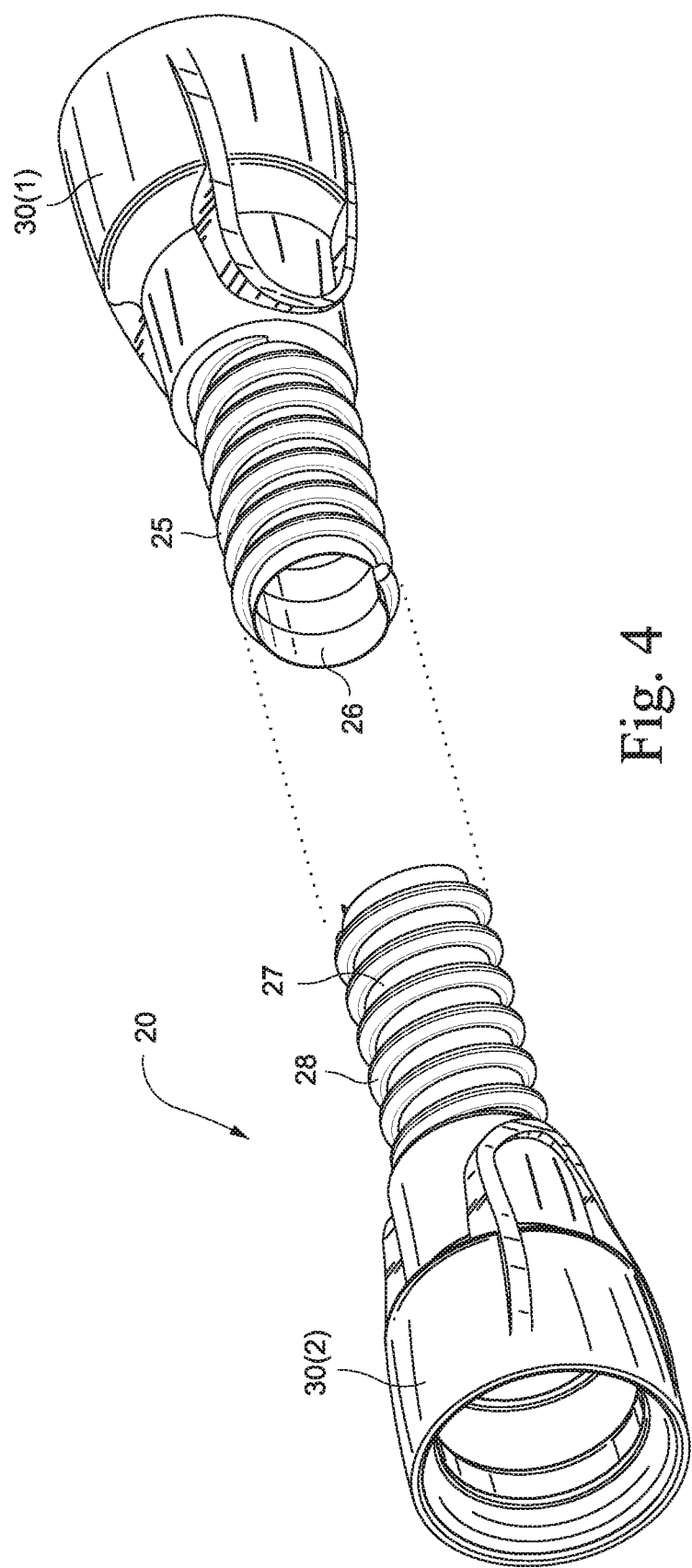
FIG. 4 is a perspective view of an non-heated air delivery conduit including cuffs according to an embodiment of the present invention.
Figure 5:
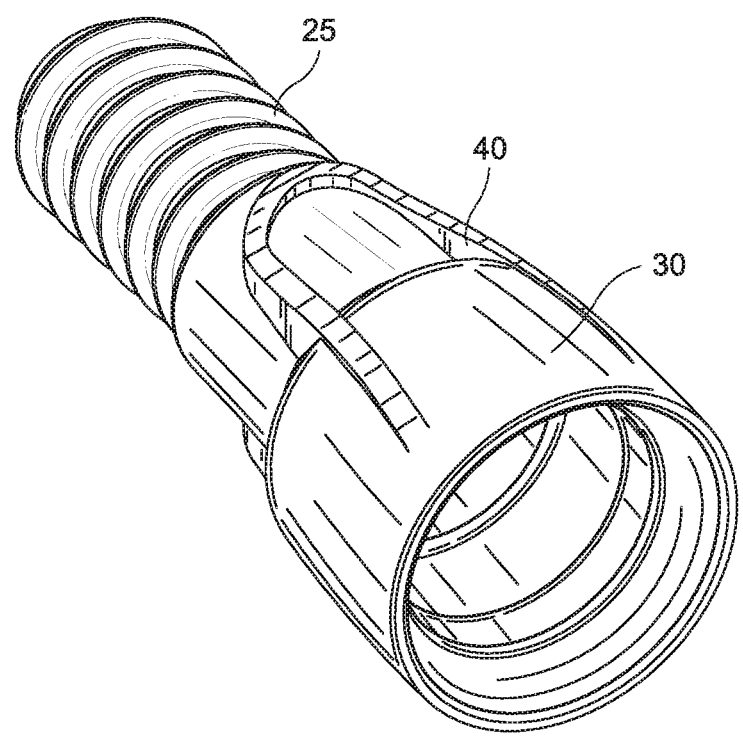
FIGS. 5 to 9 are various views of the cuff of FIG. 4.
Figure 6:
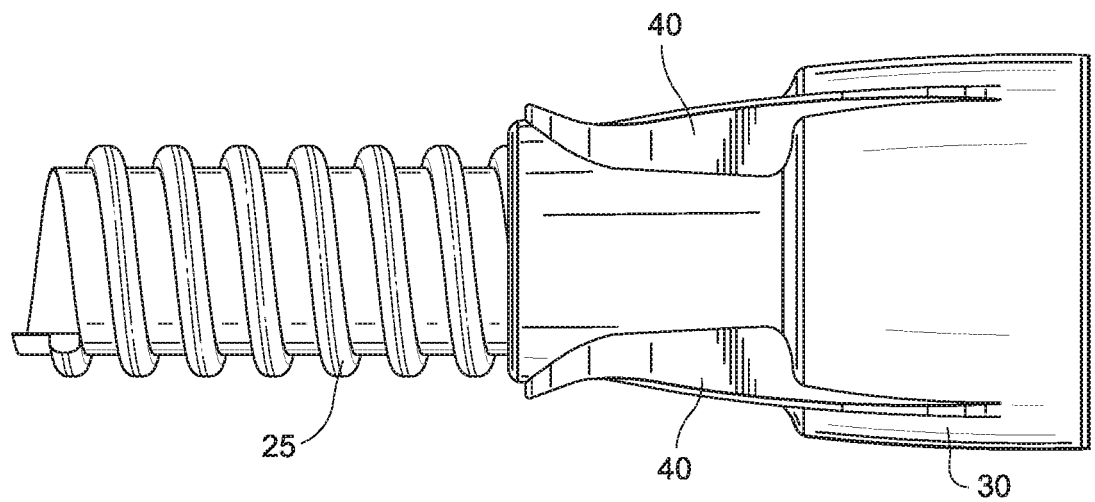
Figure 7:
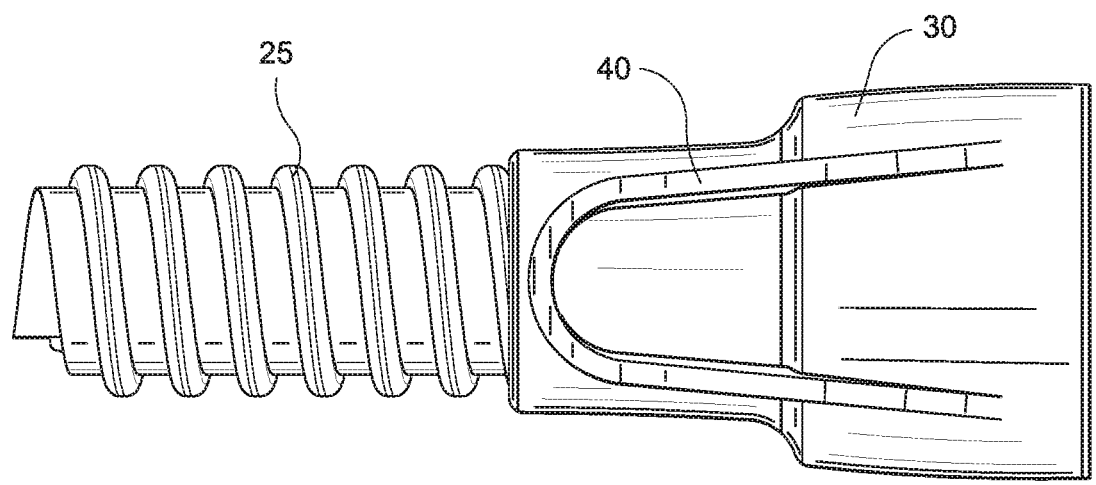
Figure 8:
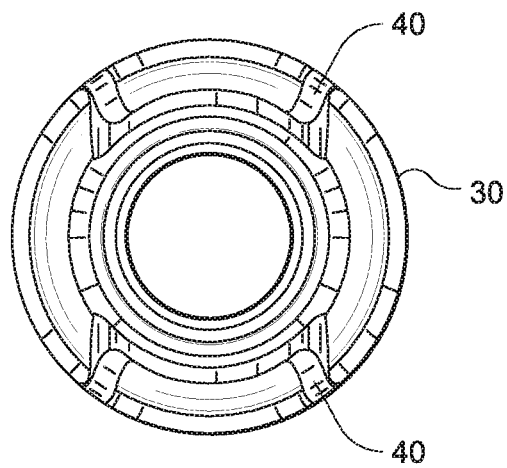
Figure 9:
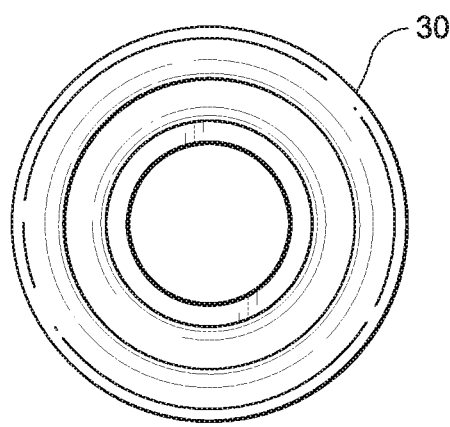

FIG. 4 illustrates an embodiment of an air delivery conduit with non-heated tubing. As illustrated, the air delivery conduit 20 includes a tube 25, a first cuff or connector 30(1) provided to one end of the tube 25 and configured and arranged to engage the outlet of the PAP device or humidifier, and a second cuff 30(2) provided to the opposite end of the tube 25 and configured and arranged to engage the inlet of the patient interface.

In the illustrated embodiment, the tube 25 has a relatively smooth interior surface 26 and an exterior surface 27 provided with flexible spiral ribbing 28. However, the interior and exterior surfaces may provide other suitable configurations, e.g., smooth exterior surface, exterior surface with disc-like annular members, etc. In an embodiment, the spiral or helix ribbing 28 has a width of about 2-3 mm, e.g., 2.5 mm, a height of about 1-2 mm, e.g., 1.5 mm, and a pitch of about 4.5 to 5.5 mm, e.g., 5.2 mm, e.g., to optimize flexibility, noise, and occlusion.

Figure 10:
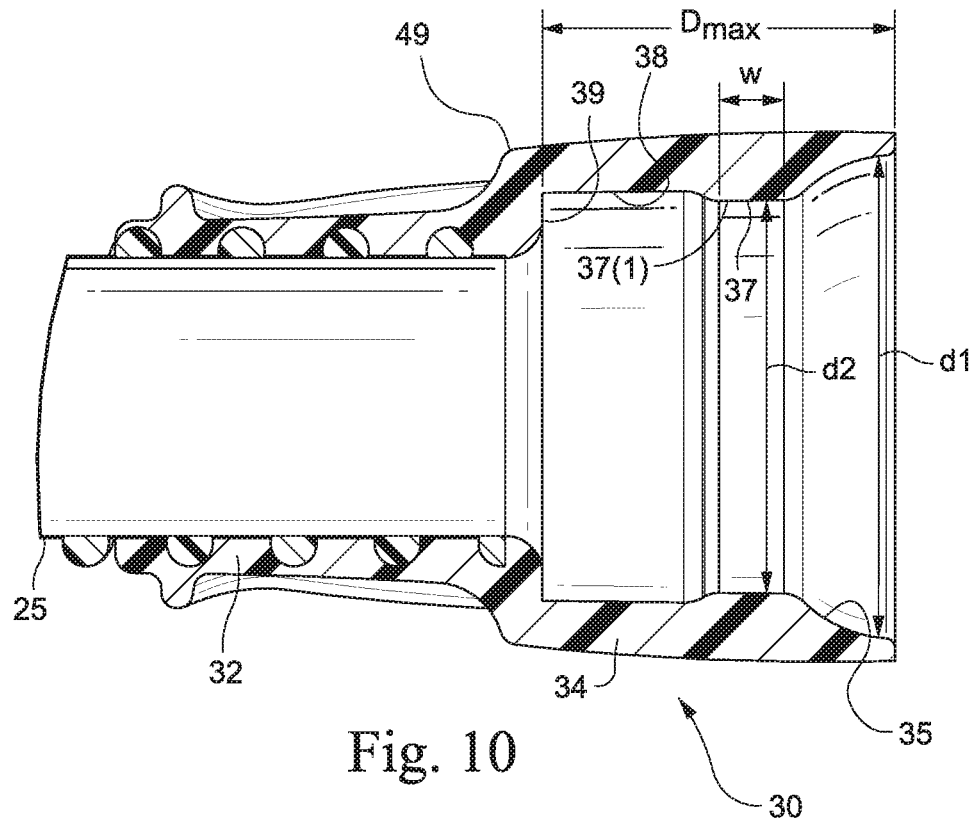
FIG. 10 is a cross-sectional view of the cuff of FIG. 4.

In this embodiment, each cuff 30(1), 30(2) is similar to one another. FIGS. 5-9 show various views of the cuff (simply indicated as 30), and FIG. 10 shows an exemplary cross-section through the cuff 30.

As illustrated, the cuff 30 includes a generally cylindrical first end portion 32 and a generally cylindrical second end portion 34. The first end portion 32 is provided (e.g., fixed, co-molded, etc.) to the tube 25 and the second end portion 34 (e.g., with a larger diameter than the first end portion) is removably connectable to a tubular connector 100 (e.g., see FIGS. 11-1 to 11-3) provided to the patient interface, PAP device or humidifier.

In an embodiment, the cuff 30 is molded of a resilient rubber-like material, e.g., TPE. The cuff may be coupled or otherwise communicated with the tube 25 in any suitable manner. For example, the cuff may be formed separately from the tube and attached thereto, e.g., friction fit, mechanical interlock, adhesive, etc. Alternatively, the cuff may be integrally formed in one piece with the tube, e.g., molding, co-molding, etc.

The interior surface of the second end portion 34 provides varying internal diameters to facilitate alignment, engagement, seal, and retention of the cuff with the tubular connector. In this embodiment, the cuffs are designed to allow connection of a 15 mm (internal diameter) tube 25 to a standard 22 mm (external diameter) ISO (International Organization for Standardization)-taper connector (e.g., see outlet connector 100 in FIG. 29) used in medical devices. Such standard or ISO-taper connector is provided to the inlet of the patient interface (e.g., in the form of an elbow end portion, elbow swivel connector, etc.) and the outlet of the PAP device or humidifier.

However, the tube and/or cuffs may have any suitable length or diameter for use in air delivery. For example, the cuffs may be adjusted to suit other connector sizes. That is, the cuffs may be structured for use with other non-"ISO" or non-"standard" connectors. For example, the cuffs may be designed to fit a 15 mm (internal diameter) tube or a 19 mm (external diameter) connector for a patient interface device. In exemplary embodiments, the cuff may be designed to interconnect a 15 mm tube to a 15 mm connector or the cuff may be designed to interconnect a 22 mm tube to a 15 mm connector. Such arrangements may advantageously reduce the weight or bulk of the connections and facilitate increased ease of movement. Also, the cuffs may be used with tubing having alternative internal diameters, e.g., tube may have internal diameter of 15 mm, 19 mm, 22 mm, etc.

2.1 Curved or Chamfered Lead-in

As shown in FIGS. 10 and 11-1 to 11-3, the second end portion 34 provides an entry surface 35 that is curved along its length to provide a curved lead in for inserting the cuff onto the connector 100. That is, the open face or opening of the cuff is flared or tapered outwardly to provide a sufficiently large entry. The curved entry surface 35 provides an internal diameter d1 that is larger than the external diameter of the tubular connector 100. The internal diameter d1 is preferably about 0.1 mm to about 10 mm, 0.5 mm to 10 mm, or more preferably 2 mm to 5 mm, greater than the external diameter of the tubular connector. For example, the internal diameter may be about 23-30 mm (e.g., about 25 mm) for use with a standard 22 mm connector. Such curved lead in and large entry diameter provided by the entry surface 35 facilitates initial alignment and engagement of the cuff 30 with the connector 100. In addition, the curved entry surface 35 leads or guides the connector 100 to the sealing and retention bead 37 of the cuff as described below.

Figure 12:
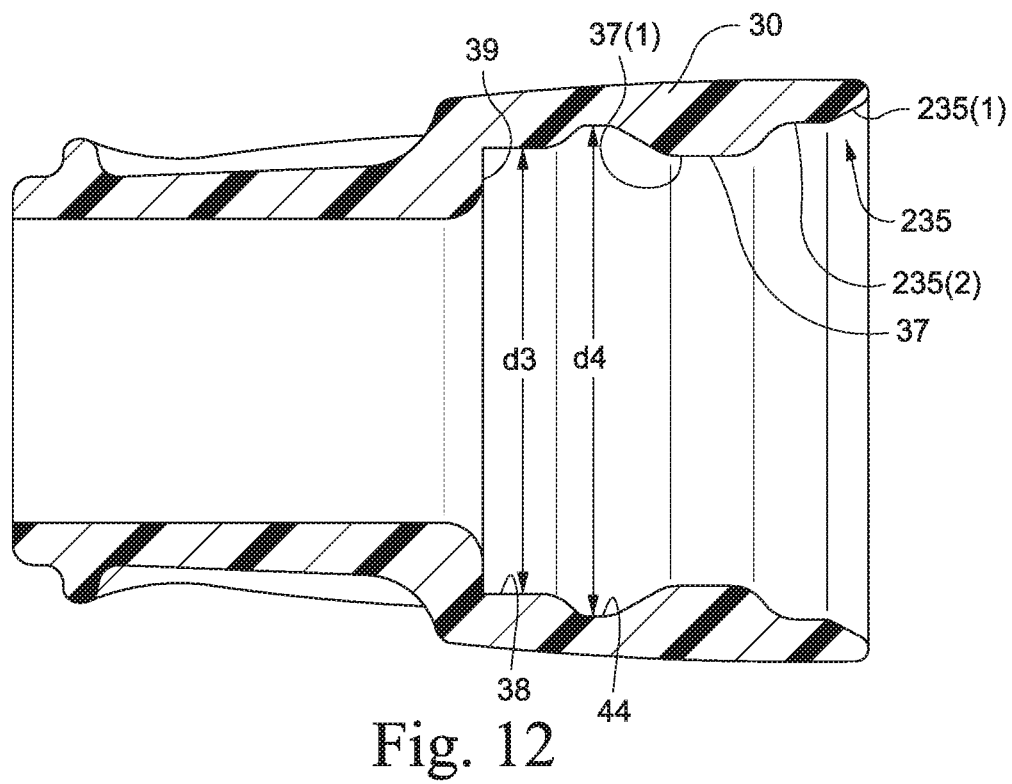
FIG. 12 is a cross-sectional view of a cuff according to an alternative embodiment of the present invention.
Figure 13:
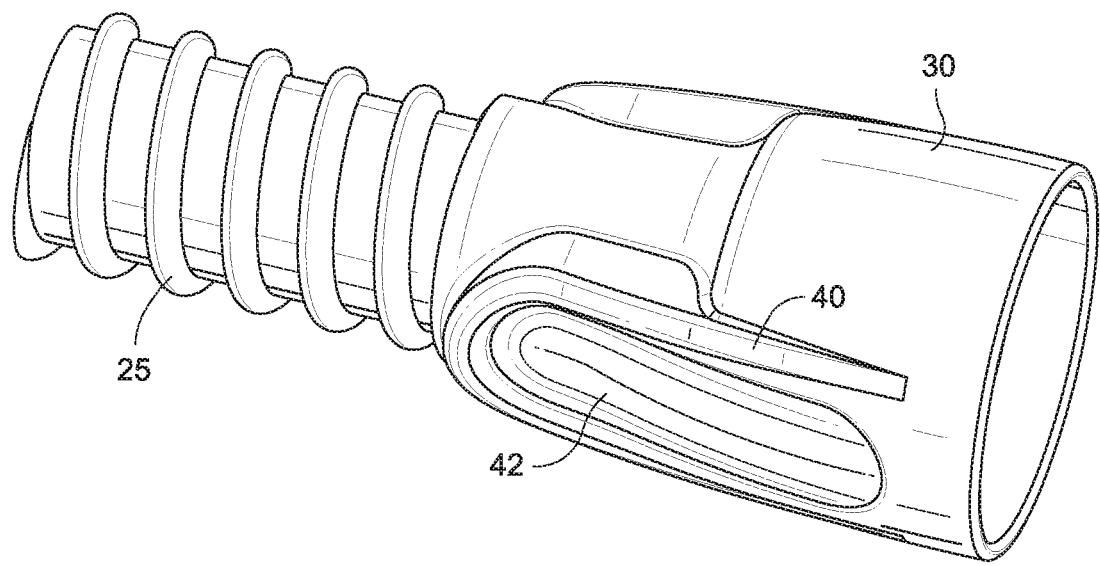
FIGS. 13 to 18 are various views of a cuff according to an alternative embodiment of the present invention.
Figure 14:
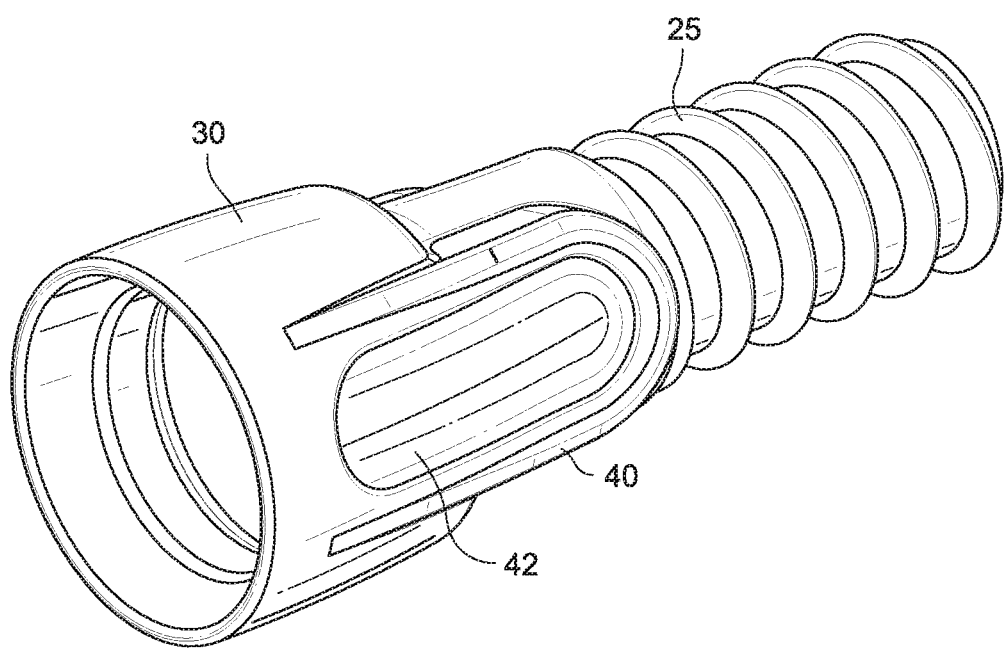
Figure 15:
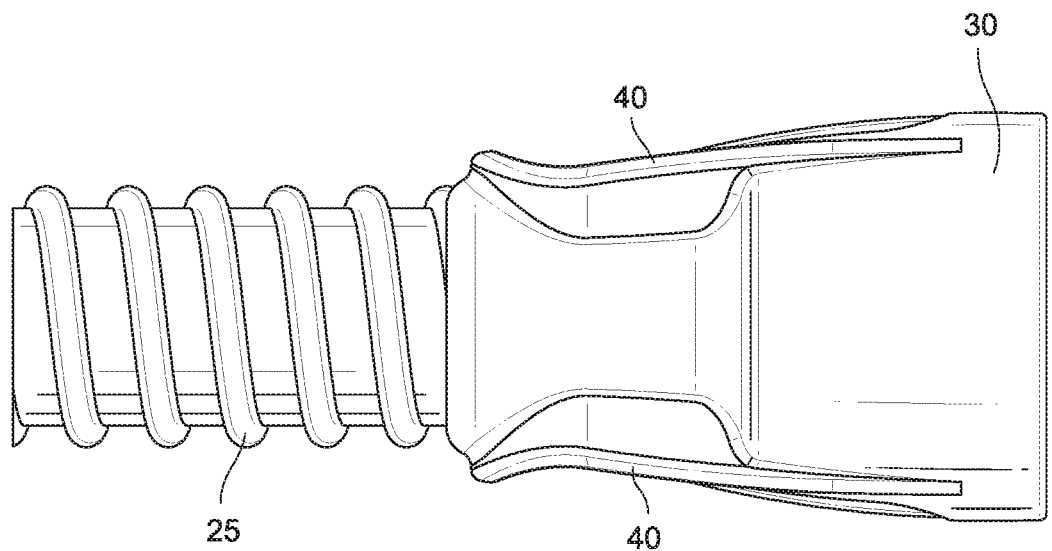
Figure 16:
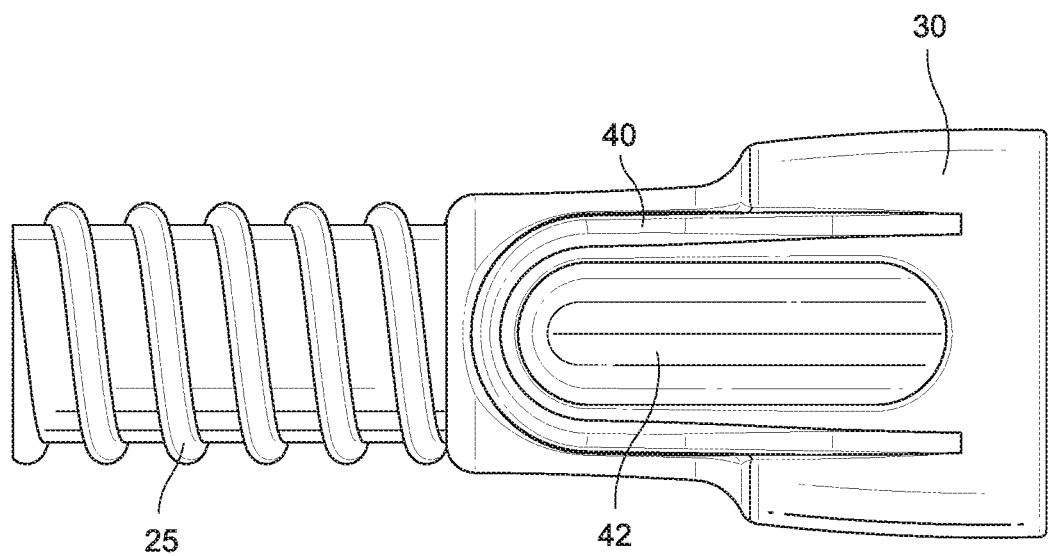
Figure 17:
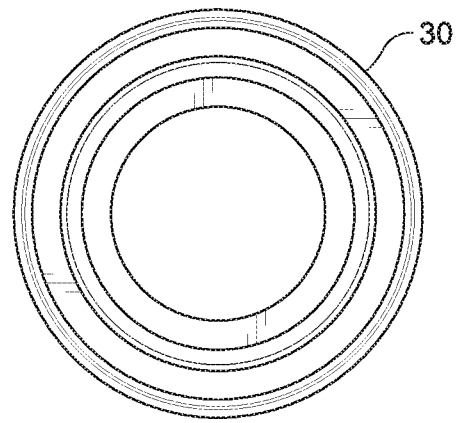
Figure 18:
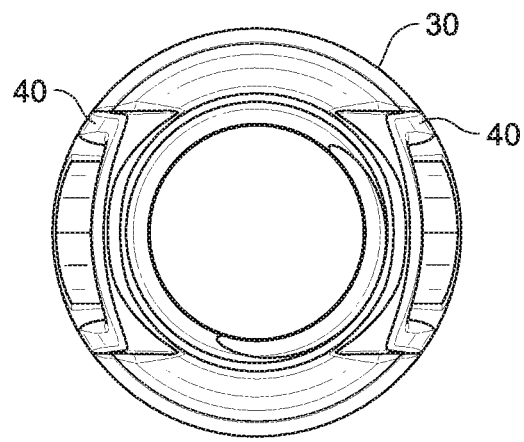

FIG. 12 shows an alternative configuration of the entry surface. In this embodiment, the entry surface 235 includes a chamfered or beveled edge 235(1) which leads to an annular interior surface 235(2). Both the edge 235(1) and interior surface 235(2) provide an entry diameter that is larger than the external diameter of the tubular connector to facilitate alignment and engagement of the cuff with the connector.

2.2 Sealing and Retention Bead

Figures 1, 11:
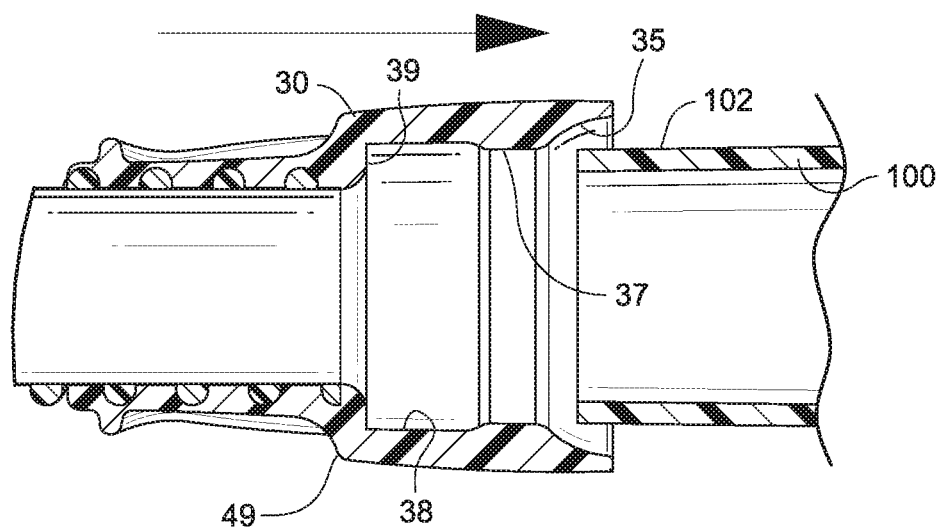
Figures 2, 11:
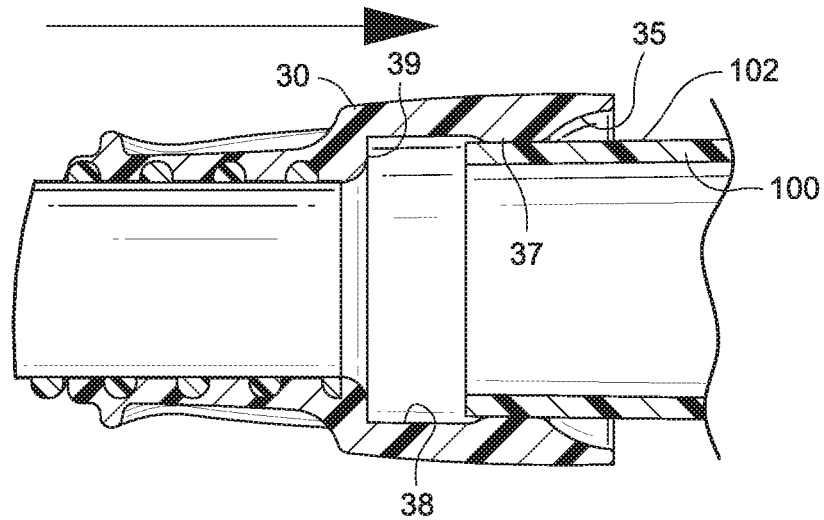
Figures 3, 11:
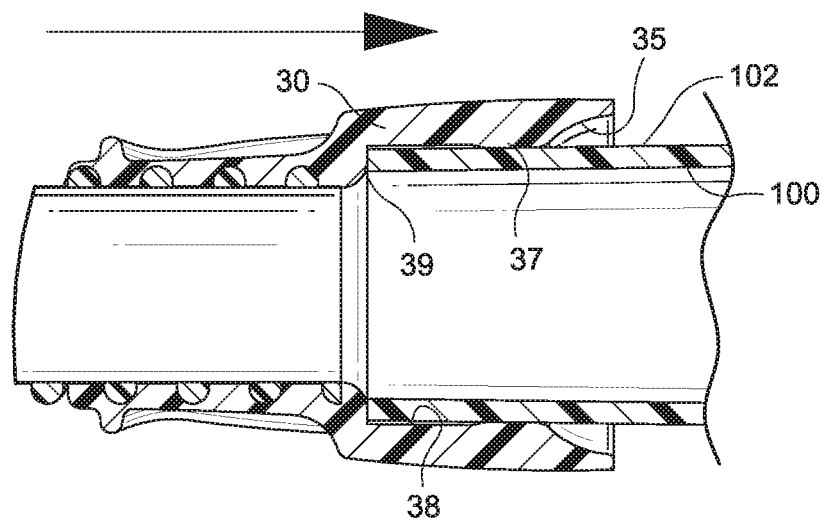

As shown in FIGS. 10, 11-1 to 11-3, and 12, the sealing and retention bead 37 is an annular bead or protrusion provided axially inwardly from the entry surface 35, 235. The bead 37 provides an intermediate internal surface 37(1) that provides an internal diameter d2 that is smaller than the external diameter of the tubular connector 100. The internal diameter d2 is preferably about 0.1 mm to about 5 mm, or more preferably less than 1 mm, less than the external diameter of the tubular connector. For example, the internal diameter may be less than about 22 mm (e.g., about 19-21 mm or less) for use with a standard 22 mm connector. As best shown in FIGS. 11-2 and 11-3, the smaller diameter of the intermediate surface 37(1) is structured to resiliently deform upon engagement with the tubular connector 100 so as to provide a gas tight seal against the exterior surface 102 of the tubular connector 100. In addition, the bead 37 engages the exterior surface 102 with a friction fit so as to retain the cuff 30 on the tubular connector 100.

As illustrated, the width w of the bead 37 is relatively small (e.g., 12 mm or less, e.g., less than about 10 mm, less than about 5 mm, about 2-5 mm or about 3.5 mm) so as to facilitate engagement and disengagement of the bead 37 with the tubular connector 100. Specifically, the bead 37 reduces the surface area in contact with the connector 100 which reduces friction thereby facilitating connection. In known cuffs, the entire length of the interior surface of the cuff is configured to engage the connector so that the force required to engage the cuff progressively increases as the surface area in contact with the connector progressively increases upon insertion. In contrast, only the bead 37 is structured to contact the connector 100 upon insertion, which bead provides a portion of the interior surface length of the cuff, which reduces the engagement/disengagement force. In addition, once the entire width of the bead 37 is engaged with the exterior surface of the connector 100, the engagement force remains fixed and does not progressively increase upon further insertion. Stated differently, the width w of the bead is less than the maximum insertion distance $D_{max}$ of the cuff (e.g., see FIG. 10), e.g., the width w of the bead is about 10-90% of $D_{max}$, e.g., less than 50% or about 25-33%.

Figure 35:
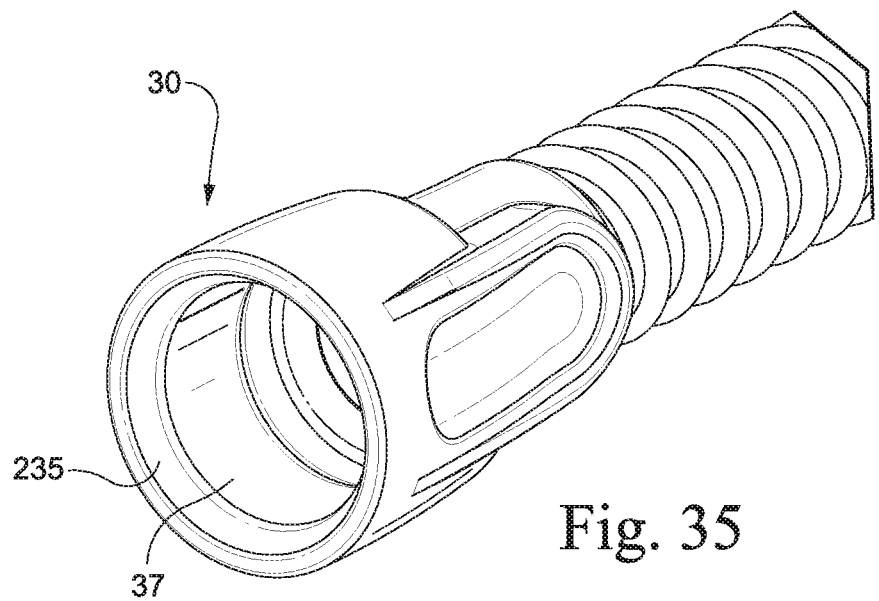
FIG. 35 is a perspective view of a cuff according to an alternative embodiment of the present invention.
Figure 36:
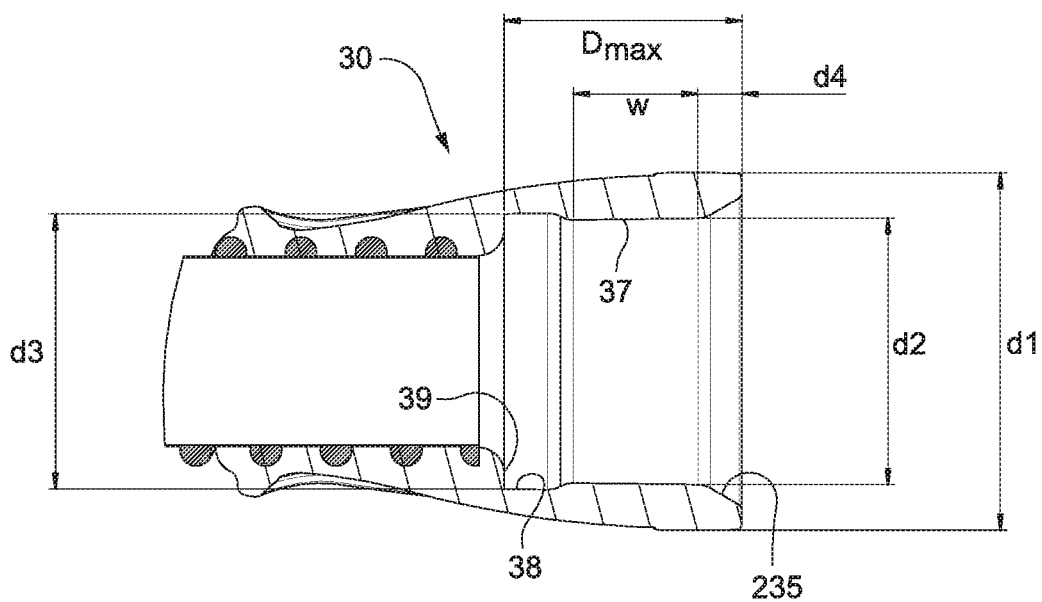
FIG. 36 is a cross-sectional view of the cuff of FIG. 35.
Figure 37:
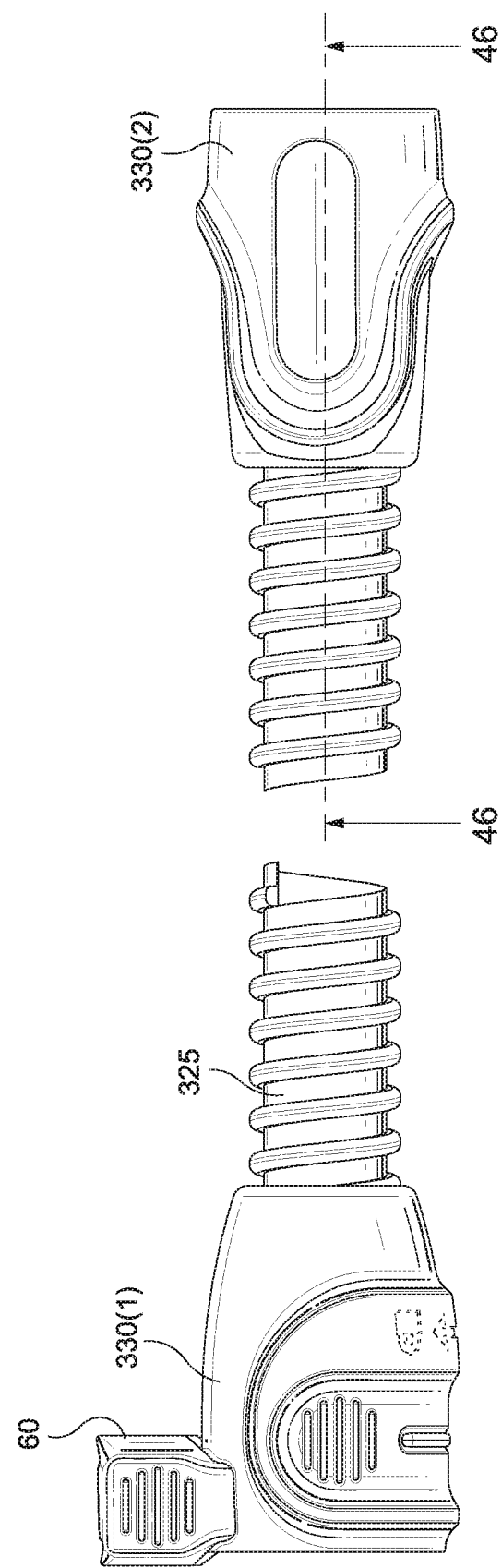
FIG. 37 is a side view of a heated air delivery conduit including cuffs according to an embodiment of the present invention.
Figure 38:
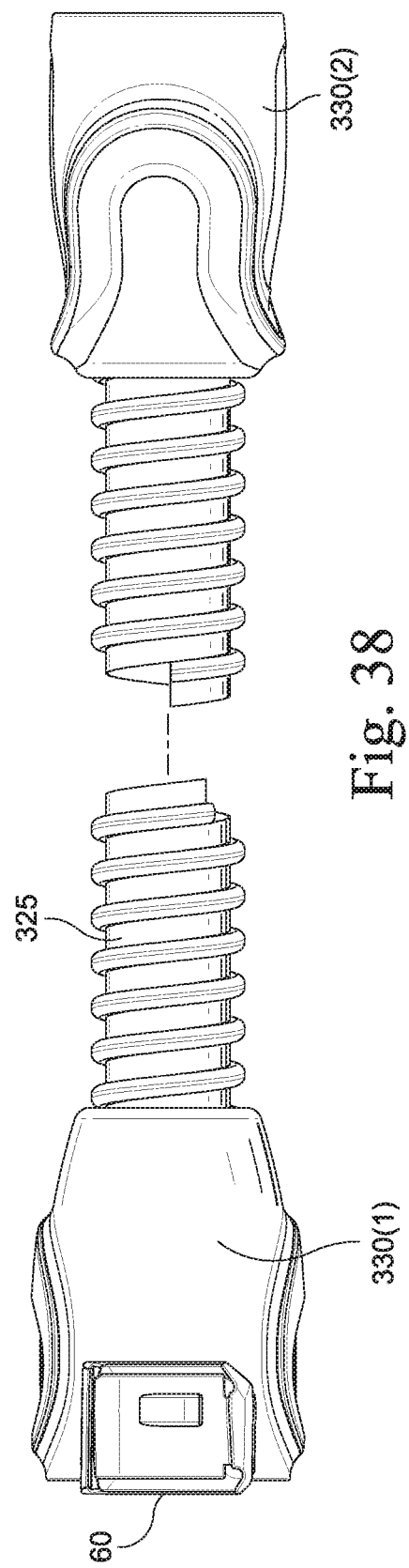
FIG. 38 is a bottom view of the conduit of FIG. 37.
Figure 39:
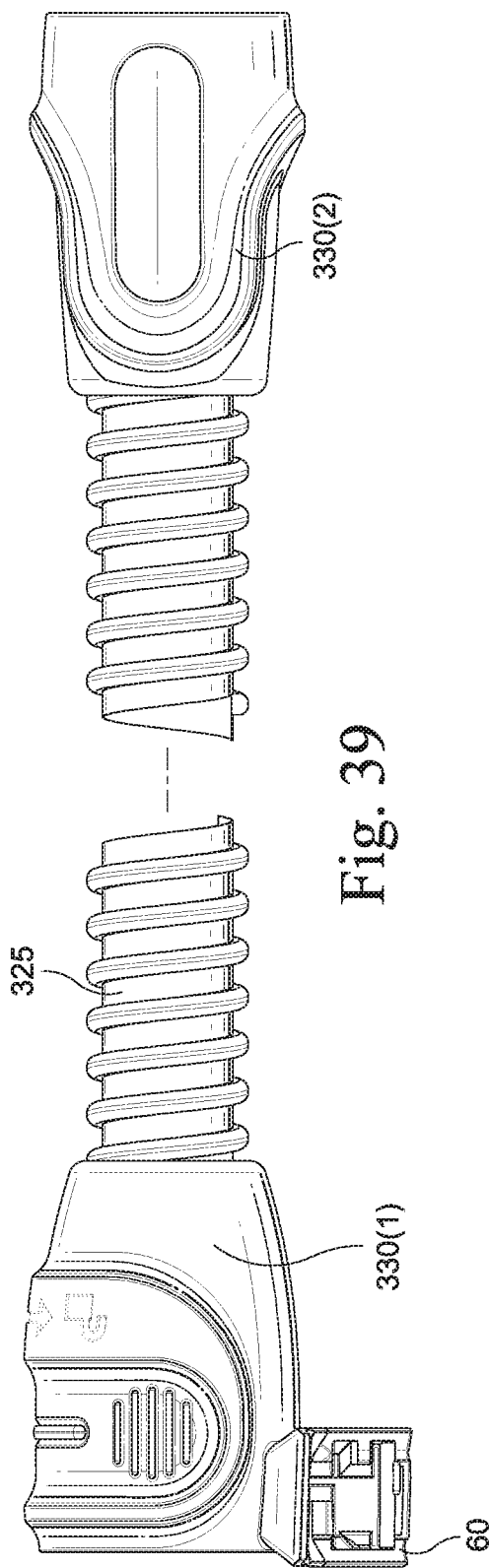
FIG. 39 is an opposite side view of the conduit of FIG. 37.
Figure 40:
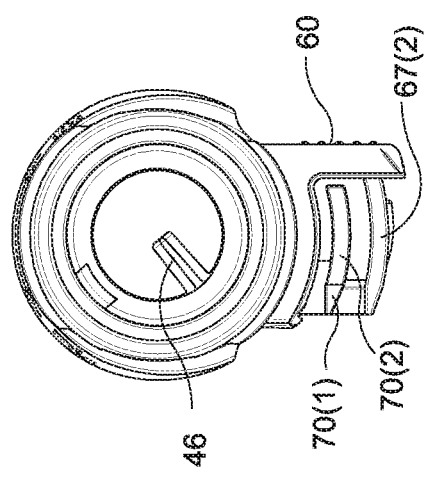
FIG. 40 is a view from the mask-end cuff of the conduit of FIG. 37.
Figure 42:
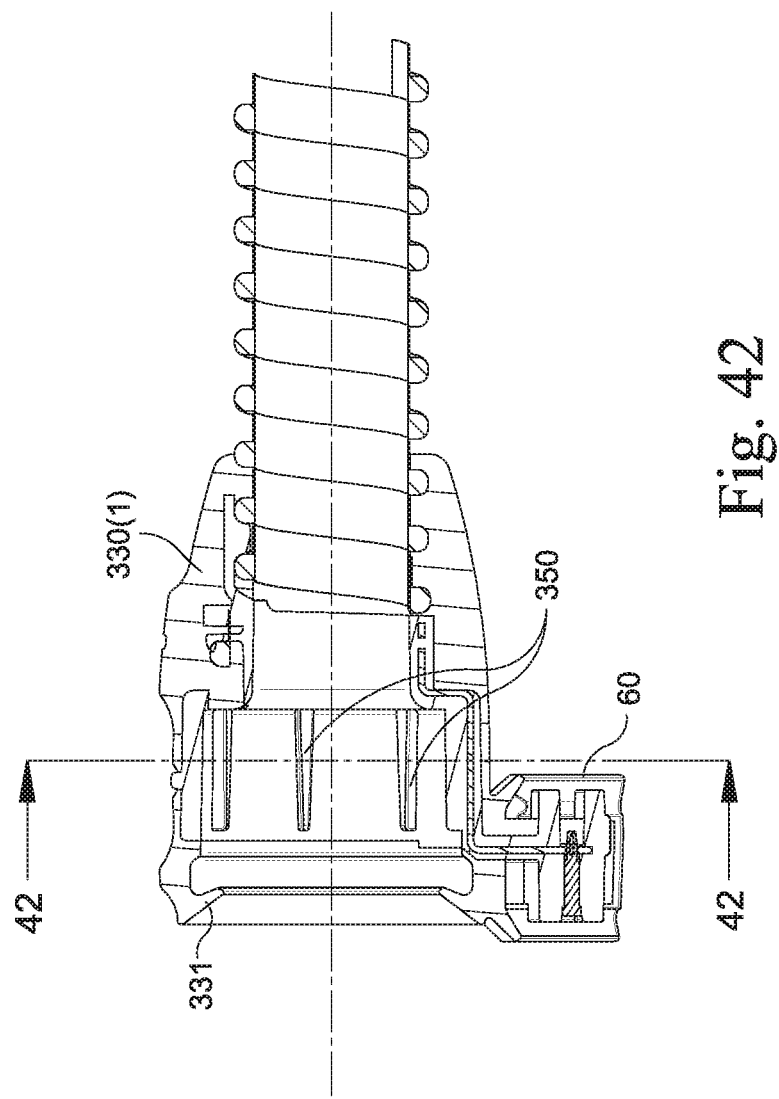
FIG. 42 is a cross-sectional view through line 42-42 of FIG. 41.
Figure 41:
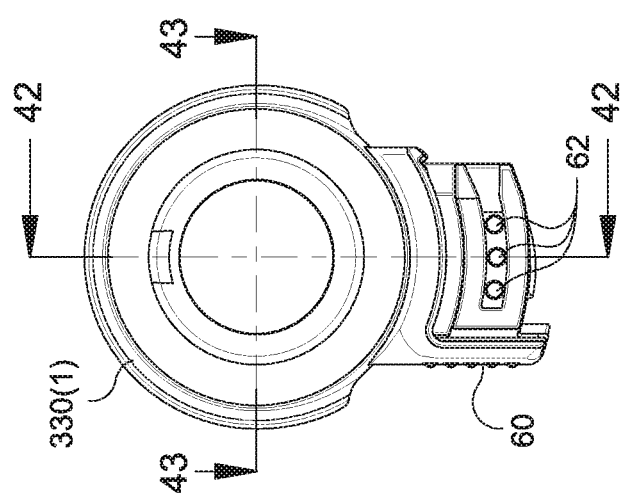
FIG. 41 is a front view of the PAP device/humidifier end cuff of the conduit of FIG. 37.

FIGS. 35 and 36 illustrate a cuff 30 including a sealing and retention bead 37 according to another embodiment of the invention. In this embodiment, the width w of the bead 37 is relatively longer than the bead shown above to enhance interference. For example, in FIG. 36, the width w is about 9-11 mm, e.g., 10 mm, and $D_{max}$ is about 18-20 mm, e.g., 19 mm. Also, in FIG. 36, diameter d1 is about 27-30 mm, e.g., 28.6 mm, and diameter d2 is about 20-22 mm, e.g., 21 mm. In an embodiment, the bead 37 may include a slight taper along its length, i.e., slightly larger diameter at the entry end of the bead. In addition, this embodiment provides a chamfered lead-in 235 to the bead, with d4 about 2.5-4.5 mm, e.g., 3.5 mm. The annular interior surface 38 provided between the bead 37 and the stop surface 39 (described in greater detail below) provides an internal diameter d3 that is substantially the same as the external diameter of the tubular connector (e.g., about 22 mm for use with a standard 22 mm connector).

Thus, the bead 37 provides a sealing and retention face to seal the cuff onto the connector and provide a retention force to prevent the cuff and tubing from accidentally being removed from the connector in use. The retention force provided by the cuff may be adjusted (e.g., by adjusting the diameter d2 and/or the width w) to meet any required standards. For example, a required standard may include the retention force being sufficient to allow the PAP device and/or humidifier to be lifted up by the air delivery conduit without the cuff disconnecting from the PAP device and/or humidifier. In an embodiment, the diameter d2 and width w provided by the bead 37 may be determined as a balance between allowing a minimal insertion force to insert the cuff onto the connector and providing sufficient retention force to meet the required standard noted above.

2.3 Stop Surface

A stop surface or flanged faced 39 is provided axially inwardly from the sealing and retention bead 37. As illustrated, the stop surface 39 extends generally transverse to the axis of the cuff so as to provide a stop to prevent the cuff 30 from inserting further onto the connector 100. In addition, the stop surface 39 provides an indication that the cuff 30 and hence the air delivery conduit 20 is fully attached to the connector 100.

2.4 Wobble Prevention

An annular interior surface 38 (e.g., see FIGS. 10, 11-1 to 11-3, and 12) is provided between the bead 37 and the stop surface 39. Such surface 38 provides an internal diameter that is substantially the same as the external diameter of the tubular connector (e.g., about 22 mm for use with a standard 22 mm connector) or slightly greater by 0.1 mm to 2 mm, between 0 to 5 mm greater, preferably up to 1 mm greater, than the external diameter of the tubular connector (e.g., about 23 mm for use with a standard 22 mm connector). In an embodiment, the internal diameter of the bead 37 when compressed by the connector may be substantially the same as the internal diameter of the interior surface 38. The width of the interior surface 38 may be greater than, less than, or equal to the width of the bead 37. In use, the interior surface 38 is positioned adjacent or near the free end of the connector 100 (e.g., see FIG. 11-3) and prevents or at least reduces any wobbling between the cuff 30 and the connector 100, while introducing little if any force necessary to overcome frictional forces opposing engagement/disengagement of the cuff.

As shown in FIG. 12, one or more grooves 44 may be provided along the interior surface 38 (and/or between the bead 37 and the interior surface 38) to reduce friction in use. That is, each groove 44 provides an internal diameter d4 that is sufficiently larger than an internal diameter d3 of the internal surface 38 so as to avoid any contact between surfaces of the groove 44 and the connector in use.

2.5 Finger Grips

The exterior surface of the cuff includes molded features in the form of grooves or finger grips to facilitate manual attachment and detachment of the cuff to and from the connector.

As shown in FIGS. 5-9, such finger grip may be a generally U-shaped protrusion 40 provided on opposing sides of the cuff and extending across the exterior surface of both the first and second end portions 32, 34 of the cuff. In an alternative embodiment, as shown in FIGS. 13-18, the cuff may be configured to provide a substantially flat surface 42 (e.g., in an ova shape) within each U-shaped protrusion 40, e.g., for raised branding. The raised branding on the surface 42 would assist in providing grip to the cuff.

In addition, the resilient material of the cuff allows the cuff to be deformed (e.g., squeezed) to assist in breaking the seal with the connector and allowing easier release of the cuff from the connector.

2.6 Single-Handed Attachment

The cuff provides an easier, single handed attachment of the air delivery conduit to the connector on the patient interface, PAP device, or humidifier as the entry surface 35 is flared or tapered outwardly to facilitate alignment and engagement and reduce the force required to insert the cuff. In an exemplary embodiment, the insertion and removal forces may be in the range of about 30 N to about 80 N. Such forces may be tunable, e.g., depending on application.

Moreover, the cylindrical configuration of the cuff and internal surfaces (e.g., bead) allows the cuff 30 to be coupled with the tubular connector 100 in any orientation. That is, the cuff 30 does not have to be rotated and/or angled with respect to the tubular connector 100 to provide a sealing engagement.

3. Cuffs for Heated Tube

Figure 19:
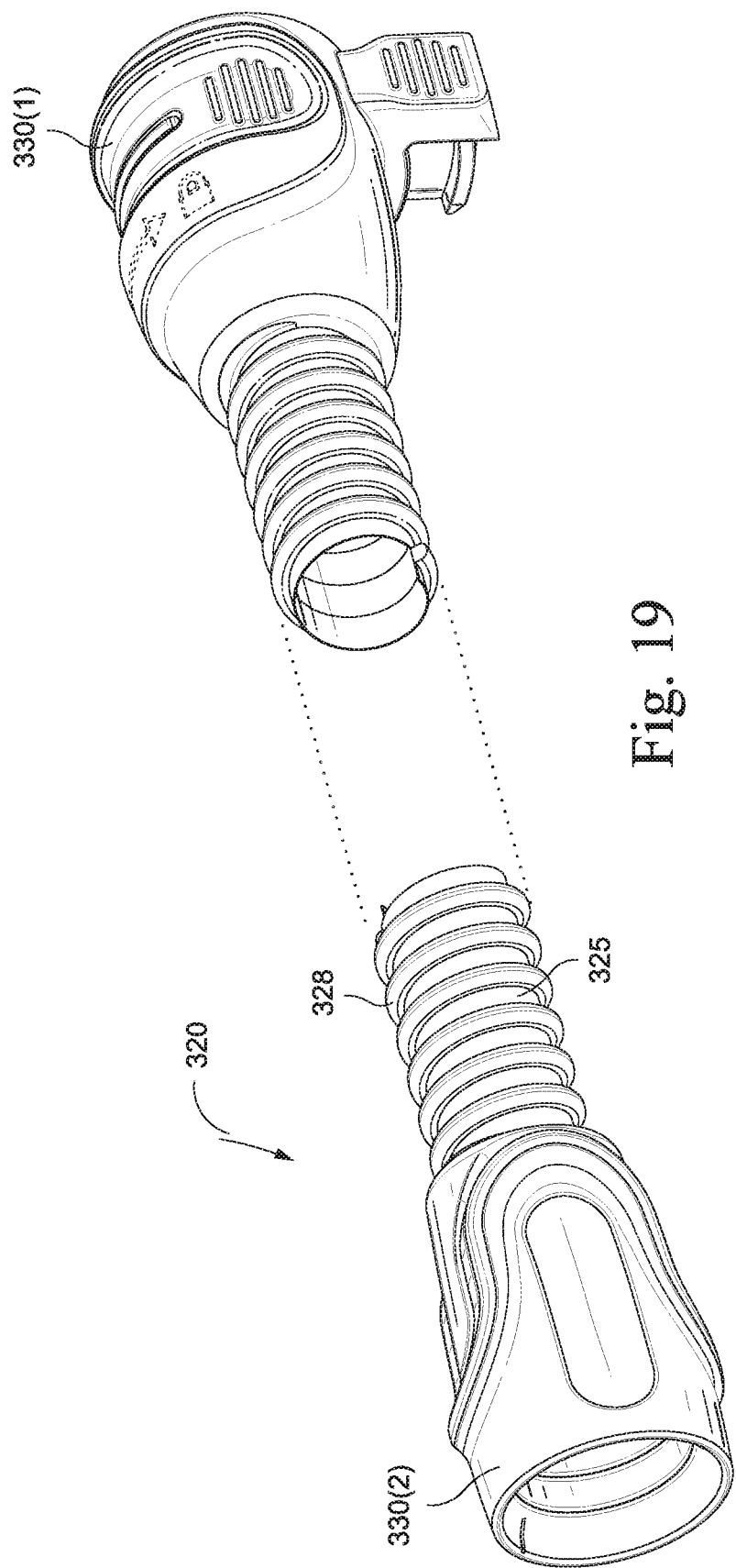
FIG. 19 is a perspective view of a heated air delivery conduit including cuffs according to an embodiment of the present invention.

FIG. 19 illustrates an embodiment of an air delivery conduit with heated tubing. As illustrated, the air delivery conduit 320 includes a tube 325, a first cuff or connector 330(1) provided to one end of the tube 325 and configured and arranged to engage the outlet of the PAP device/humidifier, and a second cuff 330(2) provided to the opposite end of the tube 325 and configured and arranged to engage the inlet of the patient interface.

In this embodiment, the tube 325 is structured to conduct heat along at least a portion of its length. For example, the spiral ribbing 328 of the tube may be structured to support one or more heated wires. In addition, the tube may be structured to support one or more sensing apparatus, e.g., flow sensor, temperature sensor, etc. Further details of such tubing are disclosed in U.S. patent application Ser. No. 11/936,822, filed Nov. 8, 2007, which is incorporated herein by reference in its entirety.

In the illustrated embodiment, the cuffs 330(1), 330(2) are different than one another as described below. However, each cuff provides structure for attaching, sealing, and retaining the cuff to the respective connector, e.g., 22 mm ISO-taper connector.

3.1 Mask End Cuff for Heated Tube

Figure 20:
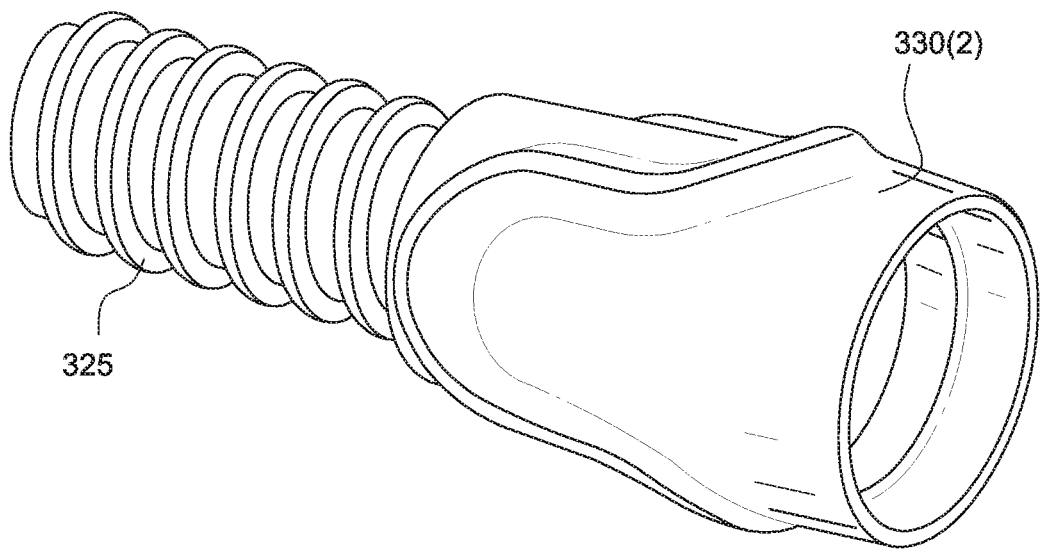
FIGS. 20 and 21 are perspective views of the mask end cuff of FIG. 19.
Figure 21:
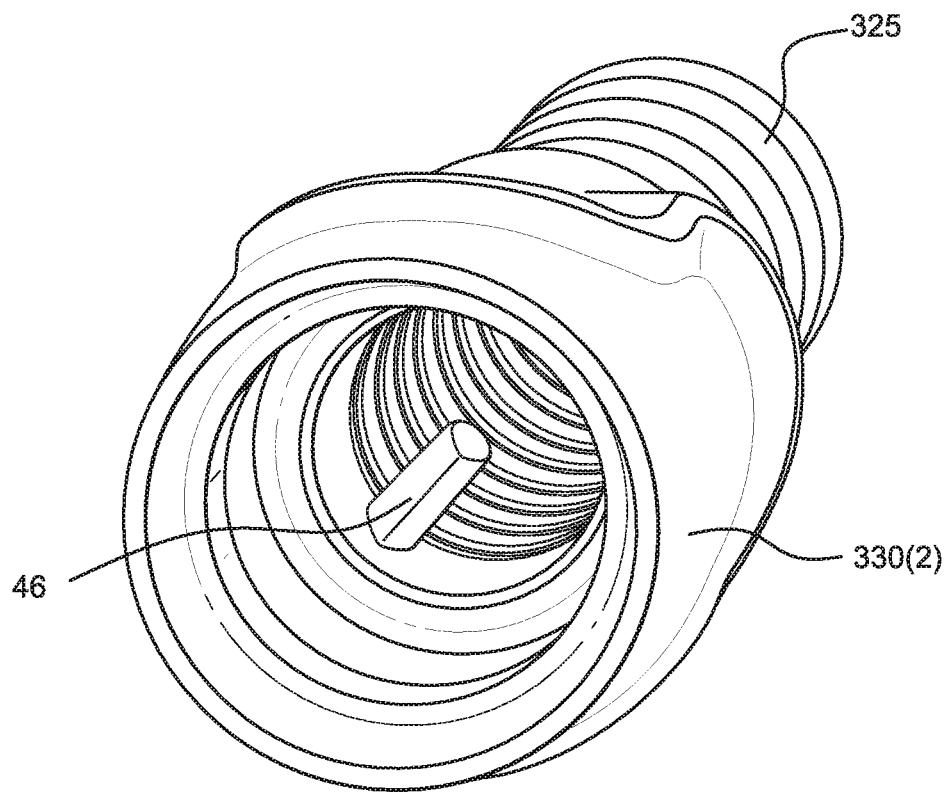
Figure 22:
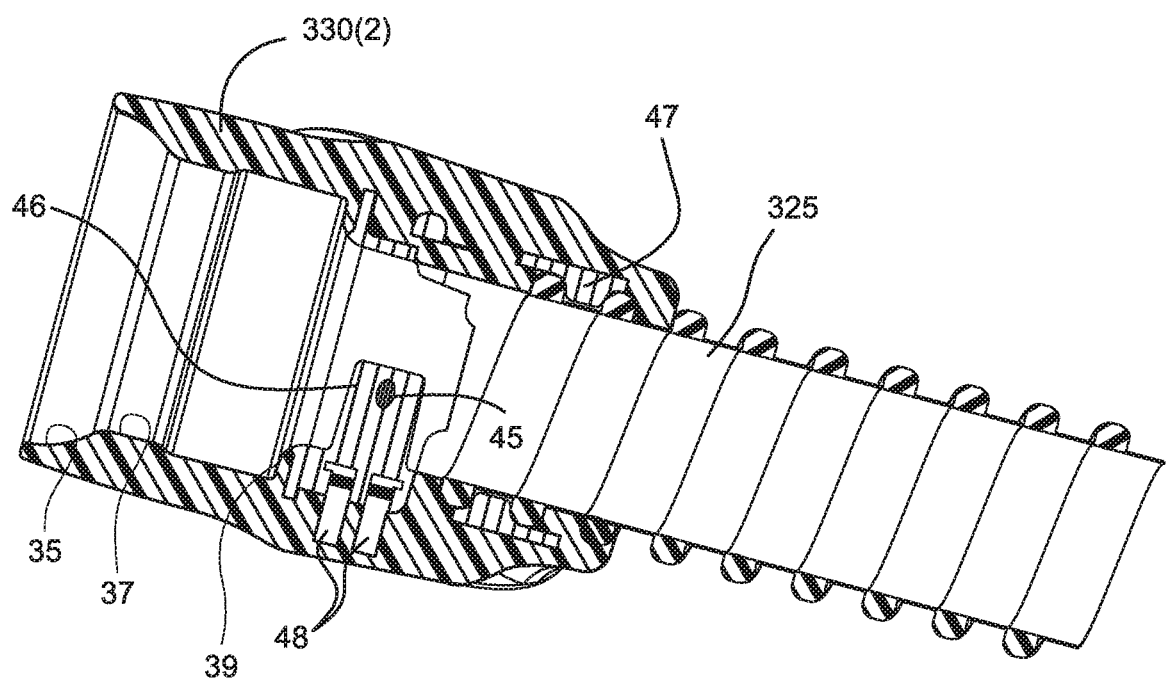
FIG. 22 is a cross-sectional view of the mask end cuff of FIG. 19.
Figure 23:
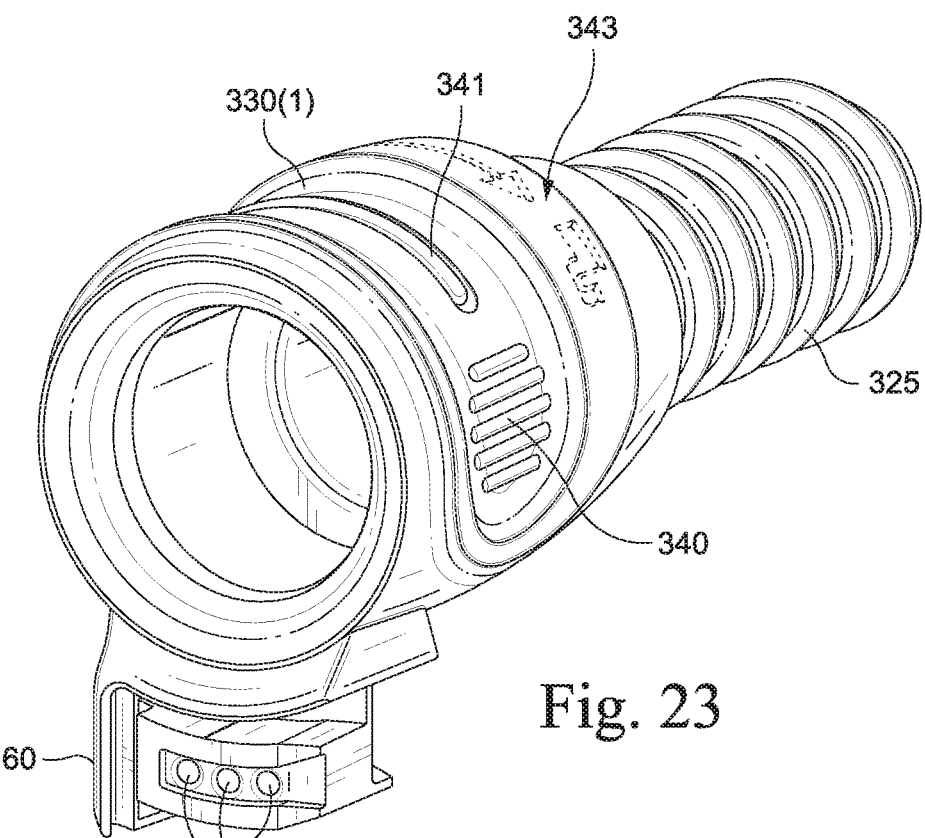
FIGS. 23 to 26 are various views of the PAP device/humidifier end cuff of FIG. 19.
Figure 24:
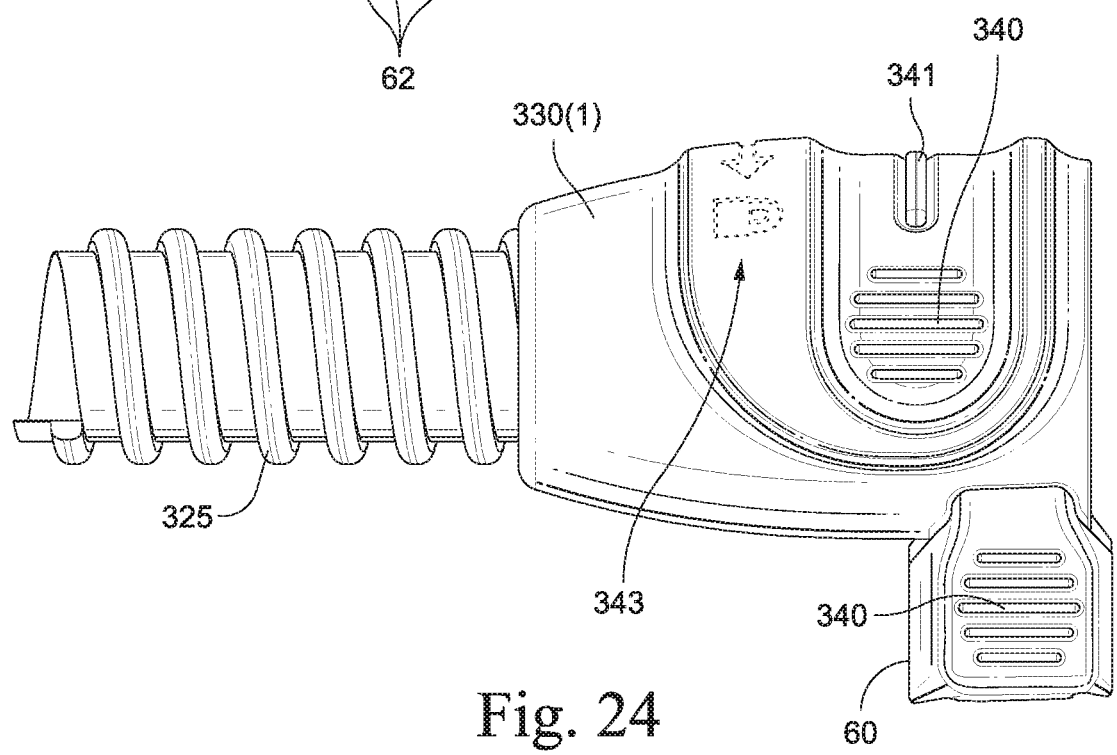
Figure 25:
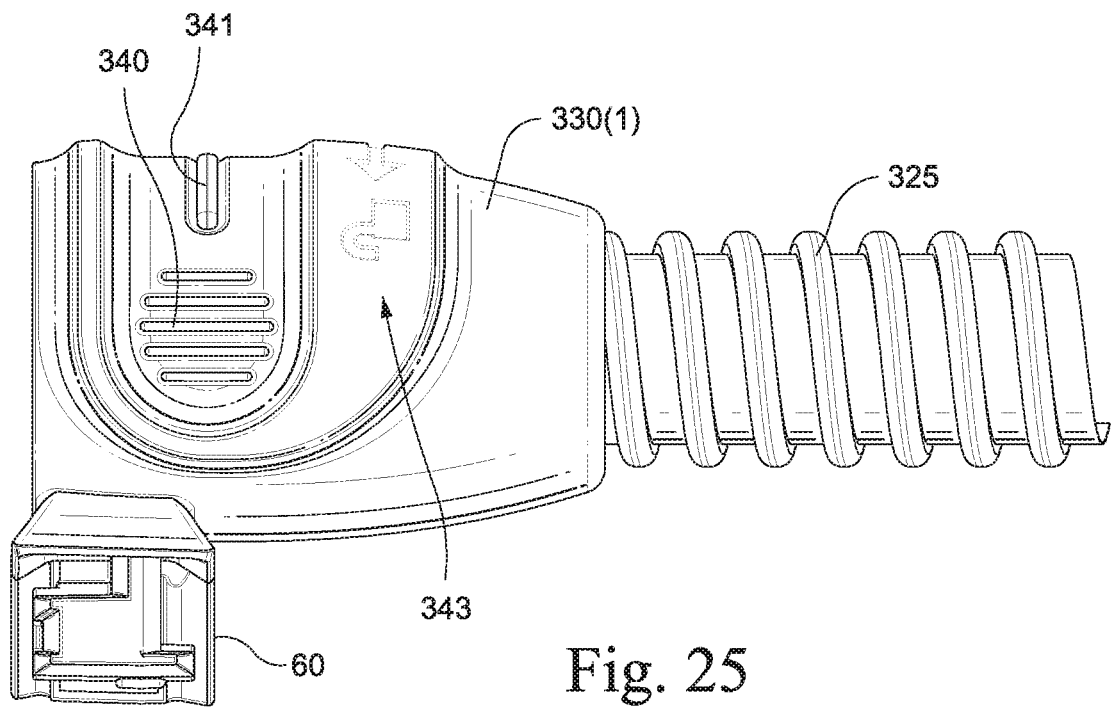
Figure 26:
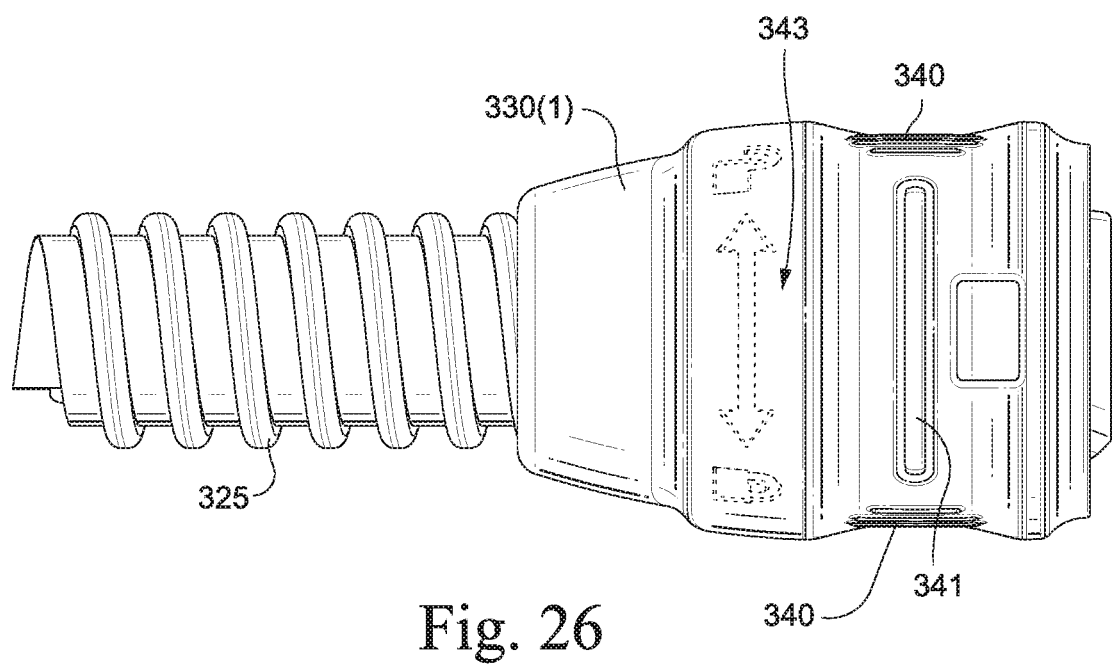

FIGS. 20-22 illustrate the cuff 330(2) structured for attachment to the patient interface or mask. The difference between the cuff 330(2) for the heated tube and the cuff 30 for the non-heated tube described above is that a thermistor 45 is located (e.g., molded into) within the rear portion of the cuff. However, the mechanism for attaching, sealing, and retaining the cuffs to the connector is substantially the same. That is, the cuff 330(2) includes a curved entry surface 35, a sealing and retention bead 37, and a stop surface 39 to aid assembly as shown in FIGS. 11-1 to 11-3 described above.

The thermistor 45 is provided to a fixture 46 within the cuff. In the illustrated embodiment, the fixture 46 is wing-shaped (e.g., see FIG. 21) to optimize convective heat transfer over a range of flow rates, while minimizing noise or pressure drop. However, the fixture 46 may have other suitable shapes and/or textures. The cuff 330(2) may be formed by, for example, overmolding on a pre-block 47, or any method disclosed, for example, in U.S. patent application Ser. No. 11/936,822, which is incorporated herein by reference in its entirety. The thermistor 45 is connected to the wires in the heated tube 325 by lead frames 48. The temperature sensed by the thermistor 45 may be provided as a signal from the thermistor 45 through the lead frames 48 and the wires to a controller located in the humidifier and/or the PAP device.

FIGS. 37-40 and 46-49 illustrate a mask-end cuff 330(2) according to another embodiment of the invention. In this embodiment, the sealing and retention bead 37 is relatively longer and a chamfered lead-in 235 is provided. The dimensions (e.g., w, $D_{max}$, d1, d2, d3, d4) of the retaining and sealing features of the cuff 330(2) are substantially similar to the cuff 30 shown in FIG. 36 and described above. The remaining features of the mask-end cuff 330(2) are substantially similar to the mask-end cuff described above and indicated with similar reference numerals (e.g., fixture 45, thermistor 45).

3.2 PAP Device/Humidifier End Cuff for Heated Tube

FIGS. 23-28 illustrate the cuff 330(1) structured for attachment to the PAP device/humidifier to establish both a pneumatic and electrical connection with the PAP device/humidifier. As illustrated, the cuff 330(1) includes an electrical connector 60 that is configured to provide an electrical connection with the PAP device/humidifier for operating heated wires provided to the tube. The electrical connector 60 includes terminals 62 that are configured to receive contacts provided to the PAP device/humidifier when the cuff 330(1) is connected to the tubular outlet of the PAP device/humidifier. Further details of such a cuff and electrical connection are disclosed in U.S. Provisional Application No. 61/097,765, filed Sep. 17, 2008, which is incorporated herein by reference in its entirety.

In this embodiment, the cuff is configured such that the seal structure for sealing against the connector is substantially independent or separate from the retaining structure for retaining the cuff on the connector.

3.2.1 Sealing

Figure 27:
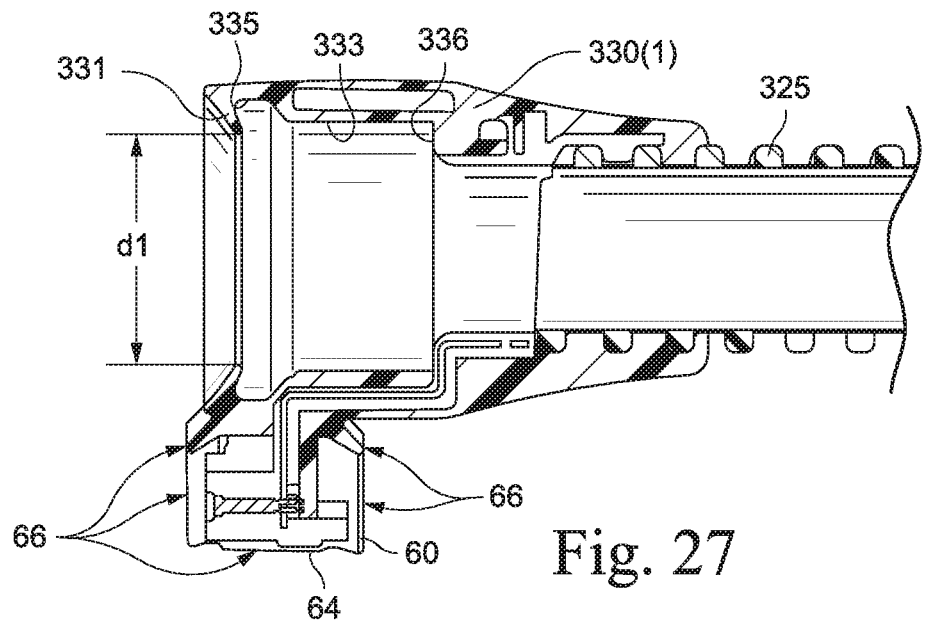
FIG. 27 is a cross-sectional view of the PAP device/humidifier end cuff of FIG. 19.
Figure 28:
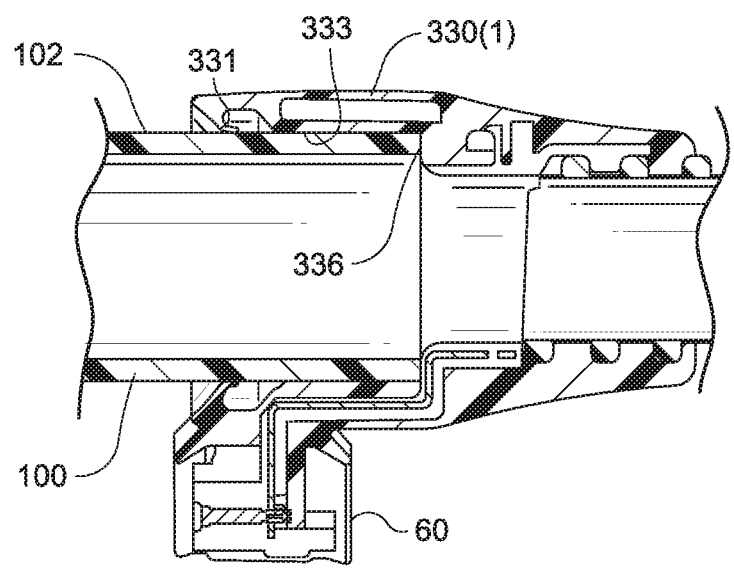
FIG. 28 is a cross-sectional view showing engagement of the PAP device/humidifier end cuff of FIG. 19 with a tubular connector.

In the illustrated embodiment, the opening of the cuff 330(1) includes a radial lip seal or sealing lip 331 along the interior surface thereof. As shown in FIG. 27, the radial lip seal 331, in its relaxed, undeformed shape, provides an internal diameter d1 that is smaller than the external diameter of the tubular connector 100. The internal diameter d1 is preferably about 0.1 mm to about 10 mm, or more preferably 1 mm to 4 mm, less than the external diameter of the tubular connector. For example, the internal diameter d1 may be less than about 22 mm (e.g., about 19-21 mm or less) for use with a standard 22 mm connector. In use, as best shown in FIG. 28, the sealing lip 331 is structured to resiliently deform upon engagement with the tubular connector 100 so as to provide a gas tight seal against the exterior surface 102 of the tubular connector 100. For example, the sealing lip 331 provides a flexible protrusion structured to resiliently deflect from a first position (FIG. 27) and into a second position (FIG. 28) within a cut-out 335.

As illustrated, the sealing lip 331 tapers outwardly towards the cuff opening to provide a sufficient lead in for aligning and engaging the cuff with the connector.

The interior surface 333 axially inwardly from the sealing lip 331 provides an internal diameter that is substantially the same as the external diameter of the tubular connector, e.g., about 22 mm for use with a standard 22 mm connector. A stop surface or flanged faced 336 within the cuff provides a stop to prevent the cuff from inserting further onto the connector 100.

In an alternative embodiment, as shown in FIGS. 42-45, the interior surface of the cuff may include a series of spaced-apart elongated protrusions or ribs 350 adapted to engage the external diameter of the tubular connector. The number and size (e.g., height, length, and/or width) of the ribs may be selected to adjust the insertion/retention force.

3.2.2 Retention

Figure 29:
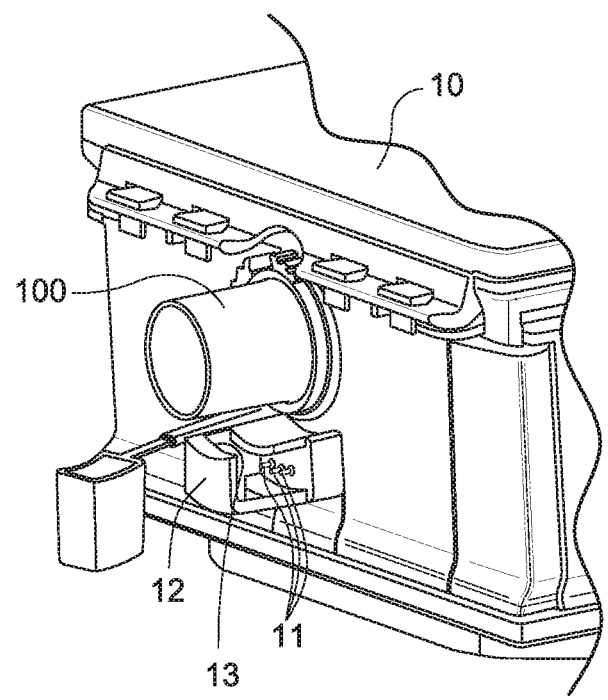
FIG. 29 is a partial perspective view of a PAP device/humidifier and the tubular connector and electrical connection portion thereof.

The electrical connector 60 provides the retention function of the cuff. Specifically, retention is via a rotate-and-lock system to align the terminals or contact surfaces 62 of the electrical connector with electrical pins 11 provided to the PAP device/humidifier (see FIG. 29). As shown in FIG. 29, the electrical pins 11 are supported within a connection portion 12 that extends outwardly from the PAP device/humidifier adjacent the outlet connector 100. The electrical connector 60 provides a heel 64 structured to be rotated into engagement with the connection portion 12 such that the heel 64 locks into a cam or recess 13 provided to the connection portion 12. When engaged, the heel 64 axially locks the cuff into place. To release, the cuff is rotated out of engagement with the connection portion to disengage the heel.

As shown in FIG. 27, a seal 66 extends from the front, back, side, and bottom of the electrical connector 60 and seals against the electrical connection portion 12 of the PAP device/humidifier 10 to prevent water spillage onto the electrical contacts.

The cuff 330(1) provides finger grips 340 along opposing sides thereof and along an edge the electrical connector 60. Also, the cuff 330(1) includes an identifying strip 341 (e.g., orange strip) to identify the tube as a heated tube. In an embodiment, a similar identifying strip may be provided to the user interface of the PAP device/humidifier and configured to illuminate or otherwise signal when the heated tube is operative, e.g., heating up, heated, etc. In addition, indicia and/or images 343 may be provided to the cuff to indicate directions for locking and unlocking the cuff with respect to the PAP device/humidifier 10.

3.2.3 Connection Angles

As noted above, the electrical connector 60 and contact surfaces 62 thereof are structured to be rotated into engagement with the electrical pins 11 supported within the connection portion 12 of the PAP device/humidifier. In order to facilitate engagement of the contact surfaces 62 with the electrical pins 11 and prevent inadvertent damage of the electrical pins 11 upon assembly (e.g., bending of the electrical pins 11), one or more contacting and/or non-contacting faces of the electrical connector 60 and/or connecting portion 12 are suitably positioned, dimensioned, and/or angled.

For example, as described below, the angle of the face may be relatively small or shallow and the length of the face may be relatively long so as to more gradually and smoothly engage the electrical connector and its contact surfaces with the connector portion and its pins. In addition, such arrangement may improve the accuracy of location.

Figure 30:
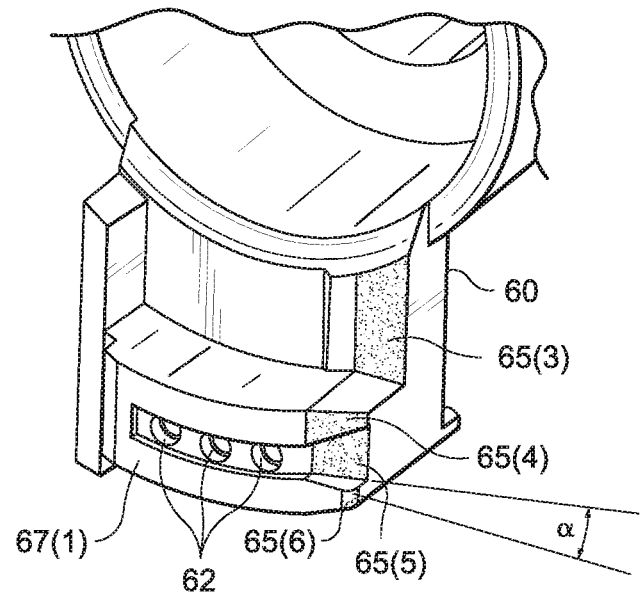
FIG. 30 is a front perspective view of an electrical connector according to an embodiment of the present invention.
Figure 31:
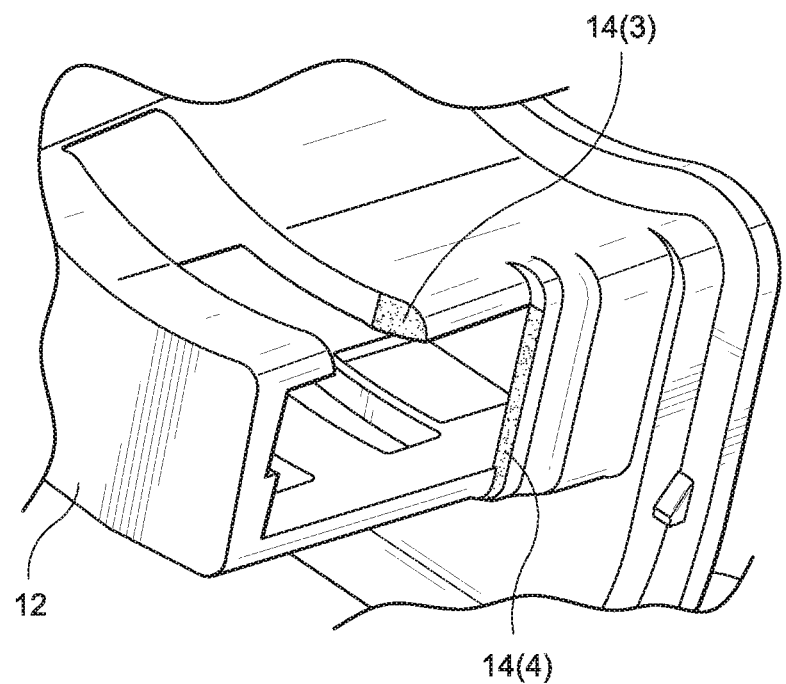
FIG. 31 is a front perspective view of a connection portion according to an embodiment of the present invention.
Figure 32:
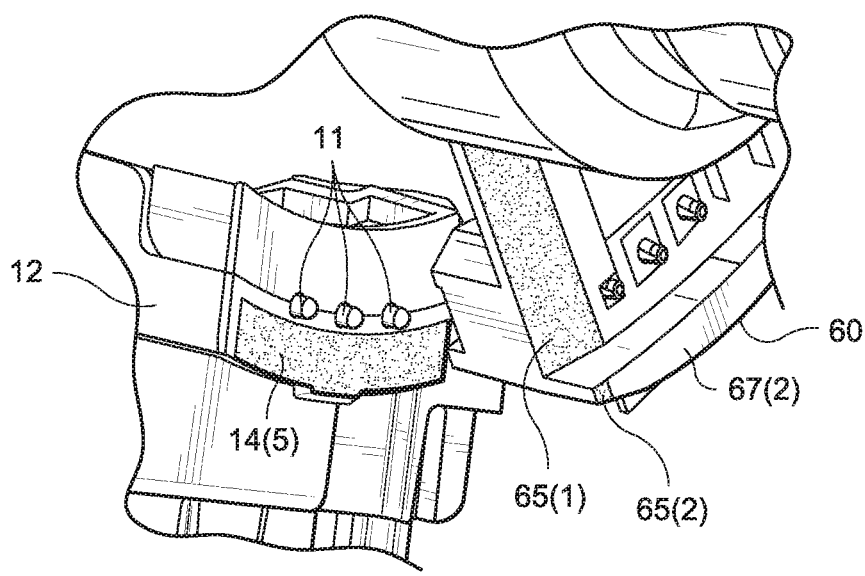
FIG. 32 is a perspective view showing the interaction between the electrical connector of FIG. 30 and the connection portion of FIG. 31 according to an embodiment of the present invention.
Figure 33:
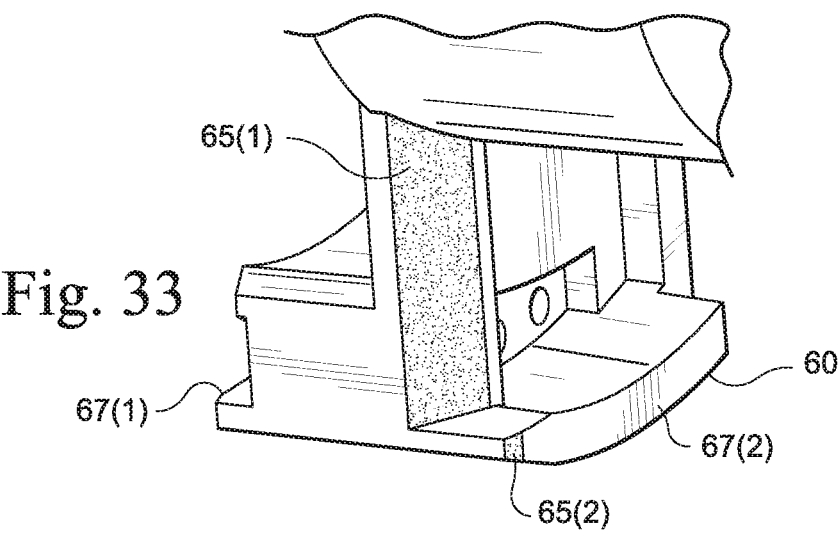
FIG. 33 is a rear perspective view of the electrical connector of FIG. 30.
Figure 34:
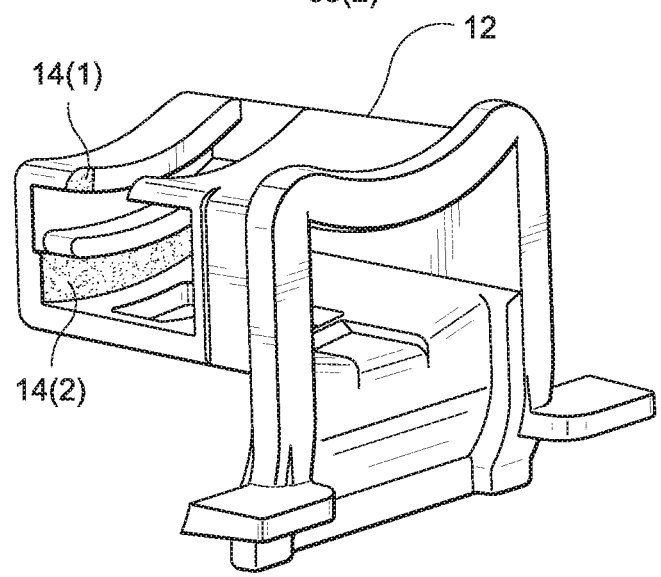
FIG. 34 is a rear perspective view of the connection portion of FIG. 31.

FIGS. 30 and 33 are front and rear perspective views of the electrical connector 60 according to an embodiment of the present invention, FIGS. 31 and 34 are front and rear perspective views of the connection portion 12 according to an embodiment of the present invention, and FIG. 32 is a perspective view showing the interaction between the electrical connector 60 and connection portion 12 according to an embodiment of the present invention.

FIGS. 32-34 best illustrate the interface between the rear or non-pin-contacting side of the connector 60 with the connection portion 12. As illustrated, the electrical connector 60 includes a vertically extending rear contact surface or rear vertical ramp 65(1) which is adapted to engage or otherwise interface with rear contact surface or rear reaction face 14(1) of the connection portion 12. Also, the electrical connector 60 includes rear contact surface or ramp 65(2) which is adapted to engage or otherwise interface with contact surface or reaction face 14(2) of the connection portion 12.

The ramp 65(1) brings the connector from about 2 mm to 0.2 mm of clearance with the connection portion 12. The ramp 65(2) brings the connector fully forward (e.g., the last 0.2 mm) into engagement with the reaction face 14(2). The ramp 65(2) is relatively short, so that the parallel front and rear faces 67(1), 67(2) are interacting or engaging before pin contact.

FIGS. 30-32 best illustrate the interface between the front or pin-contacting side of the connector 60 with the connection portion 12. As illustrated, the electrical connector 60 includes a vertically extending front contact surface or vertical lead-in 65(3) which is adapted to engage or otherwise interface with contact surface 14(3) of the connection portion 12. Also, the electrical connector 60 includes contact surfaces 65(4) and 65(5) each adapted to engage or otherwise interface with surfaces 14(4) and 14(5) of the connection portion 12. In addition, the electrical connector 60 includes contact surface 65(6) adapted to engage or otherwise interface with surface 14(5) of the connection portion 12.

The lead-in 65(3) brings the connector from about 2 mm to 0.2 mm of clearance with the connection portion 12. The contact surface or upper front lead-in 65(4) brings the connector fully forward (e.g., the last 0.2 mm) into engagement with the surface 14(5). In an embodiment, the contact surface 65(6) has a radius of about 0.5 mm to 0.6 mm, e.g., to accommodate any interference (e.g., up to about 0.4 mm interference) with the surface 14(5). The contact surface 65(6) also ensures that the pins 11 are never side loaded (e.g., bent) even if the mating surface 14(5) is skewed. As shown in FIG. 30, the surface 65(5) defines an angle α which may be 15° or under.

The surfaces 65(4) and 65(5) may not engage the surface 14(4), i.e., both clear the surface 14(4) as the connector is rotated into the connection portion. In an embodiment, the surface 65(4) may be relatively close or lightly touching so that engagement is insignificant. This arrangement ensures that the pins cannot be contacted on the side.

It is noted that the connector 60 is fully constrained within the connection portion 12 before a first one of the pins 11 is contacted. This arrangement ensures that the connector 60 is stable within the connection portion 12 before first pin contact which ensures that contact between the pins 11 and contact surfaces 62 is predictable.

Figure 44:
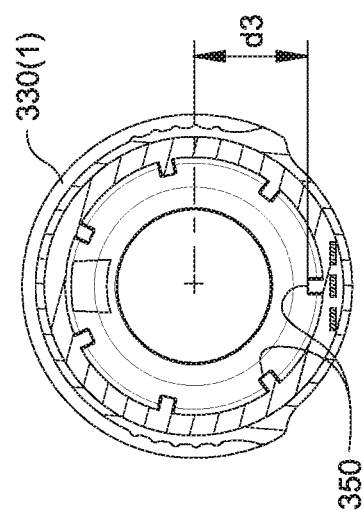
FIG. 44 is a cross-sectional view through line 44-44 of FIG. 42.
Figure 43:
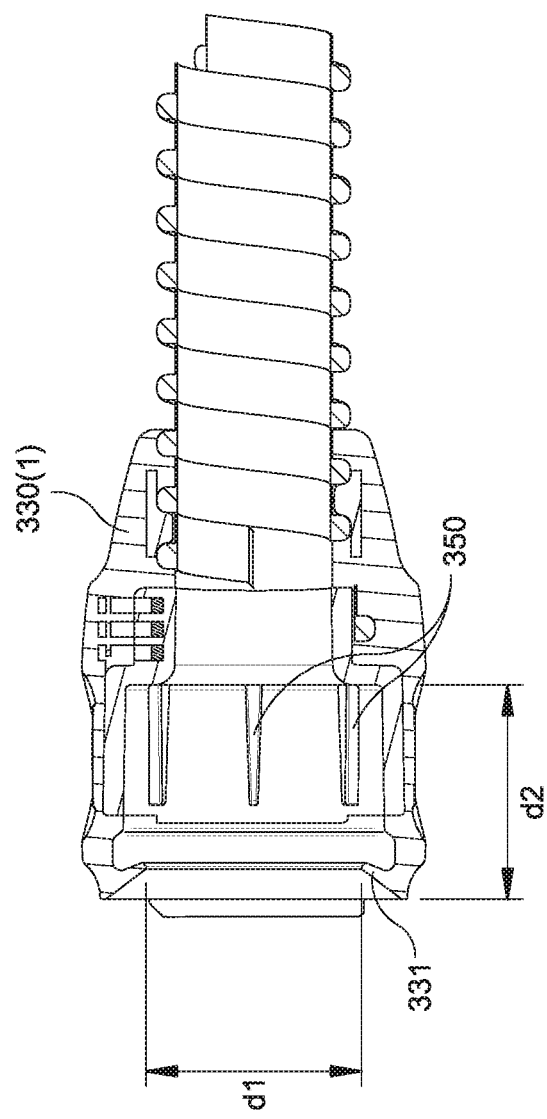
FIG. 43 is a cross-sectional view through line 43-43 of FIG. 41.
Figure 45:
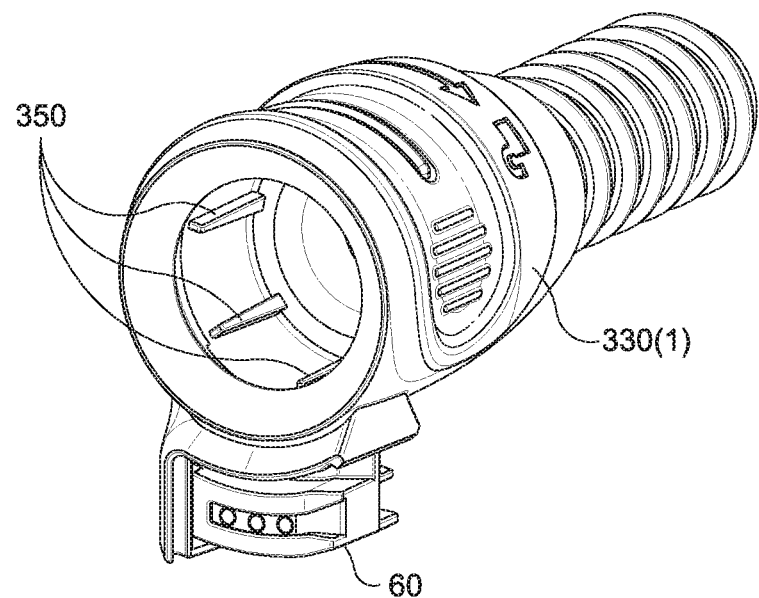
FIG. 45 is a perspective view of the cuff of FIG. 41.
Figure 46:
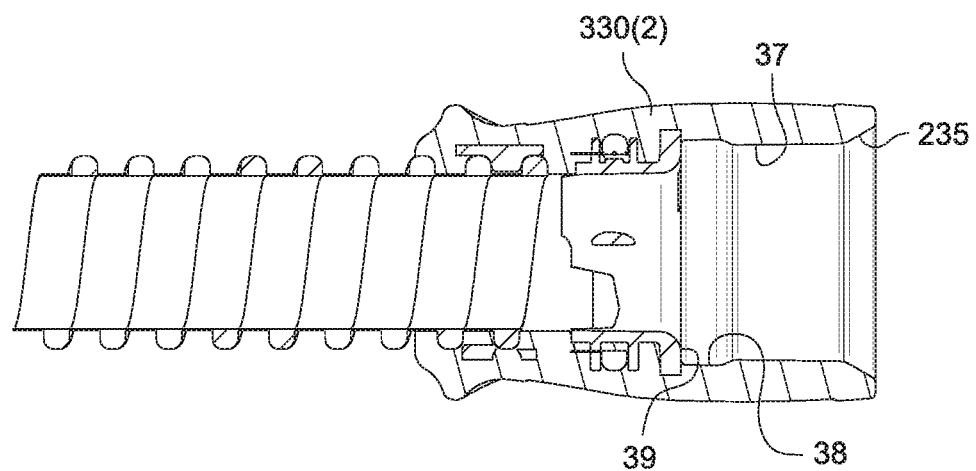
FIG. 46 is a cross-sectional view of the mask-end cuff through line 46-46 of FIG. 37.
Figure 47:
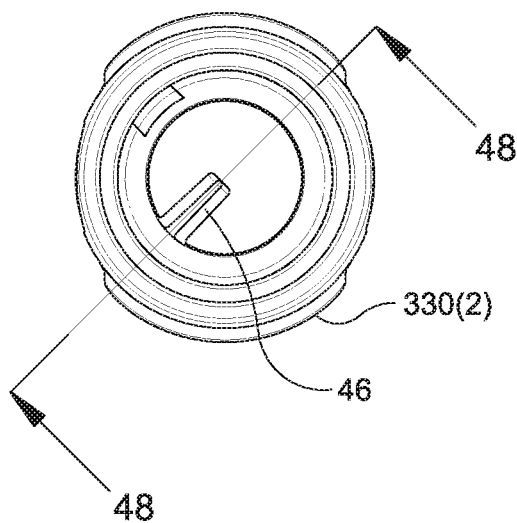
FIG. 47 is a front view of the mask-end cuff of the conduit of FIG. 37.
Figure 48:
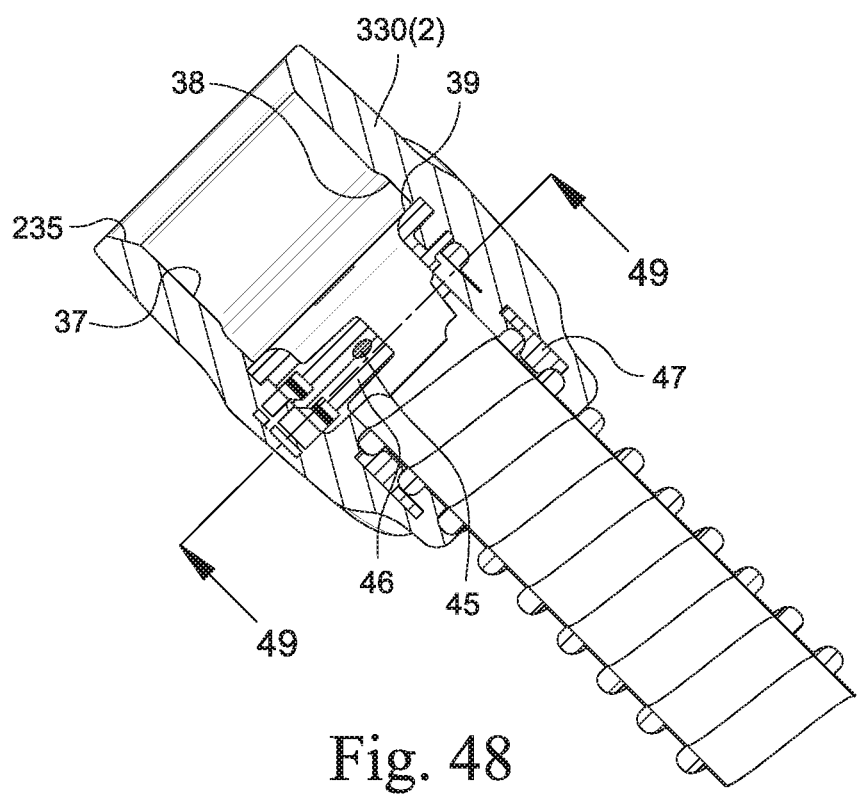
FIG. 48 is a cross-sectional view through line 48-48 of FIG. 47.
Figure 49:
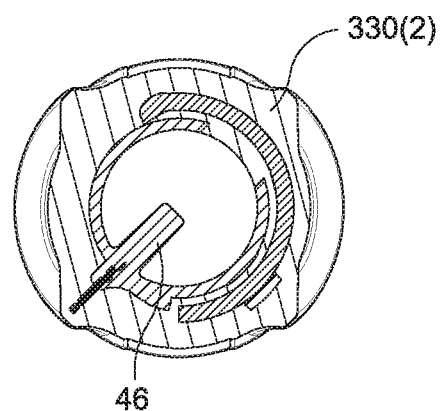
FIG. 49 is a cross-sectional view through line 49-49 of FIG. 48.

FIG. 37-45 illustrate a PAP device/humidifier end cuff 330(1) according to another embodiment of the invention. In this embodiment, the cuff includes interior ribs 350 as described above. In addition, the rear side includes a second rear face or rib 70(2) spaced upwardly from the rear face or rib 67(2), e.g., see FIG. 40. A lead-in surface 70(1) is provided to the rear face 70(2). The lead-in surface 70(1) includes similar function and dimensions as the lead-in 65(4) on the front face (but in the opposite direction). Also, in an embodiment of the cuff 330(1), as shown in FIGS. 43 and 44, d1 is about 19-22 mm, e.g., 21 mm, d2 is about 19-22 mm, e.g., 21 mm, and d3 is about 11 mm.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. Also, the various embodiments described above may be implemented in conjunction with other embodiments, e.g., aspects of one embodiment may be combined with aspects of another embodiment to realize yet other embodiments. Further, each independent feature or component of any given assembly may constitute an additional embodiment. In addition, while the invention has particular application to patients who suffer from OSA, it is to be appreciated that patients who suffer from other illnesses (e.g., congestive heart failure, diabetes, morbid obesity, stroke, bariatric surgery, etc.) can derive benefit from the above teachings. Moreover, the above teachings have applicability with patients and non-patients alike in non-medical applications.

What is claimed is:

1. An air delivery conduit for delivery of a supply of pressurized air generated by a flow generator to a patient interface for treatment of sleep disordered breathing (SDB) with continuous positive airway pressure (CPAP) therapy, the air delivery conduit comprising:
    a tube having a first end and a second end;
    a first cuff having a proximal end portion connected to the first end of the tube and a distal end portion configured to receive a tubular connector; and
    a second cuff connected to the tube at the second end,
    wherein the first cuff is constructed of an elastomeric material,
    wherein the distal end portion further comprises an entry surface, the entry surface forming an opening to receive the tubular connector,
    wherein the first cuff further comprises a longitudinal axis and an internal annular surface formed about the longitudinal axis,
    wherein the distal end portion further comprises an annular bead forming an intermediate internal surface, the annular bead extending radially inward from the internal annular surface such that an internal annular surface diameter is greater than an intermediate internal surface diameter, and the annular bead is configured to be deformed by the tubular connector to seal with an exterior surface of the tubular connector, and
    wherein when the annular bead is in an undeformed state, the intermediate internal surface has a width dimension oriented parallel to the longitudinal axis of the first cuff and the intermediate internal surface diameter is constant along the width dimension of the intermediate internal surface such that when the intermediate internal surface is in sealing engagement with the tubular connector, only the intermediate internal surface sealingly engages with the tubular connector as the first cuff is inserted onto or removed from the tubular connector.

2. The air delivery conduit of claim 1, wherein the distal end portion further comprises a stop surface positioned opposite the opening relative to the annular bead in an axial direction, the internal annular surface diameter being less than the diameter of the tubular connector at the axial position of the stop surface to resist insertion of the tubular connector beyond the stop surface.

3. The air delivery conduit of claim 2, wherein the distal end portion further comprises an annular interior surface positioned between the annular bead and the stop surface in the axial direction.

4. The air delivery conduit of claim 1, wherein the distal end portion of the first cuff has a greater external diameter than the proximal end portion.

5. The air delivery conduit of claim 1, wherein the second cuff is identical to the first cuff.

6. The air delivery conduit of claim 1, wherein the first cuff is configured to be connected to the patient interface and the second cuff is configured to be connected to the flow generator, and the second cuff further comprises an electrical connector.

7. The air delivery conduit of claim 1, wherein the width dimension is less than approximately 10 mm.

8. The air delivery conduit of claim 7, wherein the width dimension is approximately 2 mm to 5 mm.

9. The air delivery conduit of claim 1, wherein the proximal end portion further comprises a finger grip.

10. A system for treatment of sleep disordered breathing, the system comprising:
    a flow generator configured to generate the supply of pressurized air;

a patient interface configured to contact the patient's face to provide the supply of pressurized air to the patient; and the air delivery conduit of claim 1.

11. The air delivery conduit of claim 1, wherein the first cuff is structured such that once the annular bead is engaged with an exterior surface of the tubular connector along the entire width dimension of the intermediate internal surface of the annular bead, an engagement force due to friction between the first cuff and the tubular connector remains fixed and does not progressively increase upon further insertion of the tubular connector into the first cuff.

12. An air delivery conduit for delivery of a supply of pressurized air generated by a flow generator to a patient interface for treatment of sleep disordered breathing (SDB) with continuous positive airway pressure (CPAP) therapy, the air delivery conduit comprising:

a tube having a first end and a second end;
a first cuff having a proximal end portion connected to the first end of the tube and a distal end portion configured to receive a tubular connector; and
a second cuff connected to the tube at the second end,
wherein the first cuff is constructed of an elastomeric material,
wherein the distal end portion further comprises an entry surface, the entry surface forming an opening to receive the tubular connector,
wherein the first cuff further comprises a longitudinal axis and an internal annular surface formed about the longitudinal axis,
wherein the distal end portion further comprises an annular bead forming an intermediate internal surface, the annular bead extending radially inward from the internal annular surface, and the annular bead configured to be deformed by the tubular connector to seal with an exterior surface of the tubular connector, and
wherein when the annular bead is in an undeformed state, the intermediate internal surface is flat and parallel to the longitudinal axis of the first cuff and the annular bead comprises a surface at each axial side of the intermediate internal surface that increases in diameter away from the intermediate internal surface such that when the intermediate internal surface is in sealing engagement with the tubular connector, only the intermediate internal surface sealingly engages with the tubular connector as the first cuff is inserted onto or removed from the tubular connector.

13. The air delivery conduit of claim 12, wherein the distal end portion further comprises a stop surface positioned opposite the opening relative to the annular bead in an axial direction, the diameter of the internal annular surface being less than the diameter of the tubular connector at the axial position of the stop surface to resist insertion of the tubular connector beyond the stop surface.

14. The air delivery conduit of claim 13, wherein the distal end portion further comprises an annular interior surface positioned between the annular bead and the stop surface in the axial direction.

15. The air delivery conduit of claim 12, wherein the distal end portion of the first cuff has a greater external diameter than the proximal end portion.

16. The air delivery conduit of claim 12, wherein the second cuff is identical to the first cuff.

17. The air delivery conduit of claim 12, wherein the first cuff is configured to be connected to the patient interface and the second cuff is configured to be connected to the flow generator, and the second cuff further comprises an electrical connector.

18. The air delivery conduit of claim 12, wherein the intermediate internal surface has a width of less than approximately 10 mm.

19. The air delivery conduit of claim 18, wherein the intermediate internal surface has a width of approximately 2 mm to 5 mm.

20. The air delivery conduit of claim 12, wherein the proximal end portion further comprises a finger grip.

21. A system for treatment of sleep disordered breathing, the system comprising:

a flow generator configured to generate the supply of pressurized air;
a patient interface configured to contact the patient's face to provide the supply of pressurized air to the patient; and
the air delivery conduit of claim 12.

22. The air delivery conduit of claim 12, wherein the first cuff is structured such that once the annular bead is engaged with an exterior surface of the tubular connector along the entirety of the intermediate internal surface of the annular bead, an engagement force due to friction between the first cuff and the tubular connector remains fixed and does not progressively increase upon further insertion of the tubular connector into the first cuff.

23. An air delivery conduit for delivery of a supply of pressurized air generated by a flow generator to a patient interface for treatment of sleep disordered breathing (SDB) with continuous positive airway pressure (CPAP) therapy, the air delivery conduit comprising:

a tube having a first end and a second end;
a first cuff having a proximal end portion connected to the first end of the tube and a distal end portion having an opening and being configured to receive a tubular connector; and
a second cuff connected to the tube at the second end,
wherein the first cuff is constructed of an elastomeric material,
wherein the first cuff further comprises a longitudinal axis and an internal annular surface formed about the longitudinal axis, an annular bead extending radially inward from the internal annular surface, the annular bead configured to be deformed by the tubular connector to seal with an exterior surface of the tubular connector, and
wherein in an undeformed state the annular bead further comprises a central portion having a constant diameter in a direction parallel to the longitudinal axis and two side portions, each of the side portions being adjacent to the central portion at a corresponding axial side of the central portion, and the diameter of each of the side portions increasing in an axial direction away from the central portion such that when the central portion is in sealing engagement with the tubular connector, only the central portion sealingly engages with the tubular connector as the first cuff is inserted onto or removed from the tubular connector.

24. The air delivery conduit of claim 23, wherein the distal end portion further comprises a stop surface positioned opposite the opening relative to the annular bead in the axial direction, the diameter of the internal annular surface being less than the diameter of the tubular connector at the axial position of the stop surface to resist insertion of the tubular connector beyond the stop surface.

25. The air delivery conduit of claim 24, wherein the distal end portion further comprises an annular interior surface positioned between the annular bead and the stop surface in the axial direction.

26. The air delivery conduit of claim 23, wherein the distal end portion of the first cuff has a greater external diameter than the proximal end portion.

27. The air delivery conduit of claim 23, wherein the second cuff is identical to the first cuff.

28. The air delivery conduit of claim 23, wherein the first cuff is configured to be connected to the patient interface and the second cuff is configured to be connected to the flow generator, and the second cuff further comprises an electrical connector.

29. The air delivery conduit of claim 23, wherein the central portion has a width of less than approximately 10 mm.

30. The air delivery conduit of claim 29, wherein the central portion has a width of approximately 2 mm to 5 mm.

31. The air delivery conduit of claim 23, wherein the proximal end portion further comprises a finger grip.

32. A system for treatment of sleep disordered breathing, the system comprising:
   a flow generator configured to generate the supply of pressurized air;
   a patient interface configured to contact the patient's face to provide the supply of pressurized air to the patient; and
   the air delivery conduit of claim 23.

33. The air delivery conduit of claim 23, wherein the first cuff is structured such that once the annular bead is engaged with an exterior surface of the tubular connector along the entirety of the central portion of the annular bead, an engagement force due to friction between the first cuff and the tubular connector remains fixed and does not progressively increase upon further insertion of the tubular connector into the first cuff.

* * * * *